US010470986B2

(12) United States Patent
Hinman et al.

(10) Patent No.: US 10,470,986 B2
(45) Date of Patent: Nov. 12, 2019

(54) RESORCINOL COMPOUNDS FOR DERMATOLOGICAL USE

(71) Applicant: Conopco, Inc., Englewood Cliffs, NJ (US)

(72) Inventors: Andrew W Hinman, Mountain View, CA (US); Dana Davis, Mountain View, CA (US); Viktoria Kheifets, Mountain View, CA (US)

(73) Assignee: Conopco, Inc., Englewood Cliffs, NJ (US)

( * ) Notice: Subject to any disclaimer, the term of this patent is extended or adjusted under 35 U.S.C. 154(b) by 414 days.

(21) Appl. No.: 14/771,062

(22) PCT Filed: Mar. 6, 2014

(86) PCT No.: PCT/US2014/021390
§ 371 (c)(1),
(2) Date: Aug. 27, 2015

(87) PCT Pub. No.: WO2014/138471
PCT Pub. Date: Sep. 12, 2014

(65) Prior Publication Data
US 2016/0000669 A1 Jan. 7, 2016

Related U.S. Application Data

(60) Provisional application No. 61/775,384, filed on Mar. 8, 2013.

(51) Int. Cl.
| | | |
|---|---|---|
| *C07C 39/08* | (2006.01) |
| *A61Q 17/04* | (2006.01) |
| *A61Q 19/08* | (2006.01) |
| *A61Q 19/02* | (2006.01) |
| *A61K 8/34* | (2006.01) |
| *C07C 39/17* | (2006.01) |
| *C07C 39/15* | (2006.01) |
| *A61K 8/69* | (2006.01) |
| *A61K 8/70* | (2006.01) |
| *C07C 39/24* | (2006.01) |
| *C07C 39/367* | (2006.01) |
| *C07C 39/42* | (2006.01) |

(52) U.S. Cl.
CPC ............... *A61K 8/347* (2013.01); *A61K 8/69* (2013.01); *A61K 8/70* (2013.01); *A61Q 19/02* (2013.01); *C07C 39/08* (2013.01); *C07C 39/15* (2013.01); *C07C 39/17* (2013.01); *C07C 39/24* (2013.01); *C07C 39/367* (2013.01); *C07C 39/42* (2013.01); *A61K 2800/522* (2013.01); *A61Q 17/04* (2013.01); *A61Q 19/08* (2013.01); *C07C 2601/02* (2017.05); *C07C 2601/08* (2017.05); *C07C 2601/14* (2017.05)

(58) Field of Classification Search
CPC . A61K 8/347; A61K 8/69; A61K 8/70; A61K 2800/522; A61Q 19/02; A61Q 17/04;
A61Q 19/08; C07C 39/08; C07C 39/15;
C07C 39/17; C07C 39/24; C07C 39/367;
C07C 39/42; C07C 2601/08; C07C 2601/02; C07C 2601/14
USPC .......................................................... 424/59
See application file for complete search history.

(56) References Cited

U.S. PATENT DOCUMENTS

| | | | |
|---|---|---|---|
| 4,526,179 | A | 7/1985 | Salesky |
| 4,959,393 | A | 9/1990 | Torihara |
| 5,399,785 | A | 3/1995 | Miura |
| 5,449,518 | A | 9/1995 | Junino |
| 5,980,904 | A | 11/1999 | Leverett |
| 6,132,740 | A | 10/2000 | Hu |
| 6,504,037 | B2 | 1/2003 | Bradley |
| 6,828,460 | B2 | 12/2004 | Browning |
| 6,852,310 | B2 | 2/2005 | Harichian |
| 6,858,217 | B2 | 2/2005 | Kerschner |
| 6,863,897 | B2 | 3/2005 | Love |
| 6,869,598 | B2 | 3/2005 | Love |
| 6,911,562 | B2 | 6/2005 | Bhat |
| 6,933,319 | B2 | 8/2005 | Browning |
| 7,300,646 | B2 | 11/2007 | Harichian |
| 7,468,464 | B2 | 12/2008 | Harichian |
| 7,524,485 | B2 | 4/2009 | Harichian |
| 7,723,537 | B2 | 5/2010 | Harichian |
| 2004/0042983 | A1 | 3/2004 | Harichian |
| 2004/0109832 | A1 | 6/2004 | Harichian |

(Continued)

FOREIGN PATENT DOCUMENTS

| | | |
|---|---|---|
| CN | 101795733 | 8/2010 |
| EP | 0341664 | 11/1989 |
| JP | 61027909 | 2/1986 |

(Continued)

OTHER PUBLICATIONS

Fujikawa et al., "Antiseptics for foods. LXI", Kyoto Coll. Pharm., 1956, vol. 76; pp. 1438-1442; XP002725843. p. 1 to 1.
IPRP2 in PCTUS2014021390 dated Jun. 24, 2015. pp. 2 to 16.
Shimizu et al., "Inhibition of tyrosinase by Flavonoids, Stilbenes and Related 4-Substituted Resorcinols: Structure-Activity Investigations", Planta Medica, 2000, vol. 66, pp. 11-15; XP007906063. pp. 17 to 21.
Robinson et al., "Some Homologues of Resorcinol", Journal of the Chemical Society, 1934, vol. 322, pp. 1491-1498; XP008169909. pp. 22 to 29.
Search Report (Partial) in PCTUS2014021390 dated Jul. 17, 2014. pp. 1 to 6.

(Continued)

*Primary Examiner* — Adam C Milligan
(74) *Attorney, Agent, or Firm* — Ellen Plotkin

(57) ABSTRACT

Provided herein are methods and compositions comprising resorcinol derivatives for the use of treating, regulating or preventing a skin condition characterized by oxidative stress or a degenerative process. Methods of preventing, lightening or reducing the appearance of visible discontinuities of the skin resulting from skin pigmentation, skin aging, or other disorders are also disclosed.

5 Claims, No Drawings

(56) References Cited

U.S. PATENT DOCUMENTS

2008/0131382 A1  6/2008  Unilever
2010/0215594 A1* 8/2010  Huber ..................... A61K 8/44
                                                      424/59

FOREIGN PATENT DOCUMENTS

| JP | 3284612 | 12/1991 |
| JP | 07025742 | 1/1995 |
| JP | 7187989 | 7/1995 |
| JP | H7316034 | 12/1995 |
| JP | 10265322 | 10/1998 |
| JP | 2896815 | 5/1999 |
| JP | 2000327557 | 11/2000 |
| JP | 2001010925 | 1/2001 |
| JP | 2001163759 | 6/2001 |
| JP | 2001181173 | 7/2001 |
| RU | 2240343 | 11/2004 |
| WO | WO9915148 | 4/1999 |
| WO | WO2004052329 | 6/2004 |
| WO | WO2004052814 | 6/2004 |
| WO | WO2004052827 | 6/2004 |
| WO | WO2004069221 | 8/2004 |
| WO | WO2004080939 | 9/2004 |
| WO | WO2006097223 | 9/2006 |
| WO | WO2014138471 | 9/2014 |

OTHER PUBLICATIONS

Search Report in PCTUS2014021390 dated Oct. 10, 2014. pp. 7 to 12.
Written Opinion 2 in PCTUS2014021390 dated Feb. 5, 2015. pp. 13 to 22.
Written Opinion in PCTUS2014021390 dated Oct. 10, 2014. pp. 23 to 33.
Kim et al., "Tyrosinase inhibitors from natural and synthetic sources: structure, inhibition mechanism and perspective for the future", CMLS Cellular and Molecular Life Sciences, 2005, vol. 62, pp. 1707-1723; XP019200794 . pp. 34 to 50.

\* cited by examiner

RESORCINOL COMPOUNDS FOR DERMATOLOGICAL USE

CROSS-REFERENCE TO RELATED APPLICATIONS

This patent application claims priority benefit of U.S. Provisional Patent Application No. 61/775,384, filed Mar. 8, 2013. The entire contents of that application are hereby incorporated by reference herein.

TECHNICAL FIELD

Provided herein are cosmetic and dermatological compositions, such as resorcinol derivatives, with anti-aging, skin even-toning, and other useful properties for skin treatment.

BACKGROUND

Natural-looking skin is influenced by a number of physiological and genetic factors. Standard definitions of beautiful skin include skin having a transparent quality with uniform undertones of color and no visible or tactile discontinuities. The basis for this natural-looking appearance is in the skin structure itself. The outer layer of human skin is a semi-transparent layer known as the stratum corneum. The transparency of the stratum corneum permits glimpses of the deeper layers of skin, where blood vessels and pigments reside. The pale reddish hue of the blood vessels' hemoglobin, and the brown/black hue of melanin that is the primary skin pigment, combine to produce the skin's color. Ideal skin should also be smooth and even, with no apparent surface flaws in addition to having the transparent look with uniform color distribution.

Skin is composed of a top layer, the epidermis, which is approximately 20 cell layers or about 0.1 mm in thickness, and a lower layer, the dermis, which is from about 1 to about 4 mm in thickness and contains small blood vessels, collagen, elastin and fibroblasts. The dermis provides structural support and nutrients to the epidermis. Aging has been shown to increase cellular heterogeneity of the epidermal layer. Aging does not affect the number of cell layers in the epidermis, but the overall thickness decreases. The supporting dermis is known to thin with age and exposure to the sun and environmental contaminants. The dermal layer provides the support and blood supply for the epidermis, therefore the dermal layer is important in maintaining the elasticity and appearance of the skin.

Considerable effort has been expended to find ways to prevent adverse changes in the skin brought about by ultraviolet (UV) exposure and other causes. Preventative approaches include physically blocking or absorbing the UV radiation before it can enter the skin using UV absorbing compounds. Skin problems in aging individuals can result from a variety of extrinsic or intrinsic factors such as harmful UV radiation from the sun, exposure to the environment, stress, fatigue, disease, or a combination thereof.

Many people at different stages of their life are concerned with the degree of pigmentation of their skin and may wish to reduce the skin darkening, or may wish to lighten or even-tone their natural skin color. The mechanism by which skin pigmentation is formed, melanogenesis, is particularly complex and schematically involves the following main steps: Tyrosine→L-Dopa→Dopaquinone→Dopachrome→Melanins. The first two reactions in this series are catalyzed by the enzyme tyrosinase. The activity of tyrosinase is promoted by the action of a-melanocyte stimulating hormone or UV rays. It is well established that a substance has a depigmenting effect if it acts directly on the vitality of the epidermal melanocytes where melanogenesis normally occurs and/or if it interferes with one of the stages in melanin biosynthesis. Pigmentation disorders can take a variety of forms like hyperpigmentation, hypopigmentation, and uneven pigmentation, and include but are not limited to melasma (mask of pregnancy or chloasma), liver spots (which often develop with age) and leukoderma such as vitiligo. Some of the pigmentation occurs as a side effect of birth control pills, as a result of skin damage such as a persistent result of acne, burns, bites and other skin injuries, as after-burn scars, as cicatrical spots, as stretch mark scars, and as dark circles and puffiness under and around the eyes. The degree of pigmentation disorders of the skin in many cases increases with the age of the individuals. Because of the involvement of tyrosinase in melanogensis, tyrosinase inhibition assays are often used to screen potential skin lightening agents. Some mushroom tyrosinases (such as that from *Agaricus bisporus*) are homologous with mammalian tyrosinase, and mushroom tyrosinase is often used in inhibition assays due to its ready commercial availability. However, the enzyme inhibition assays may not be as good an indicator of activity as assays which are more similar to the intended clinical or cosmetic use, such as the MatTek Corporation's MelanoDerm™ Skin Model (a system which consists of normal, human-derived epidermal keratinocytes and melanocytes formed into a multilayered model of human epidermis).

In the United States, the most commonly used treatment for hyperpigmentation is 1,4-benzenediol, which is known as hydroquinone. Treatment with hydroquinone interferes with the action of tyrosinase, which is an enzyme used in the synthesis of melanin, and compositions are sold across the counter at about 2% hydroquinone and by prescription at higher concentrations. Hydroquinone compositions are effective but have some undesirable side effects. These can be burning, redness, sensitization and irritation in some patients. U.S. Pat. No. 4,526,179 refers to certain hydroquinone fatty esters that have good activity and are less irritating and more stable than hydroquinone. Japanese Patent Application No. 27909/86 (JP 61-27909) refers to other hydroquinone derivatives that do not have the drawbacks of hydroquinone but that have relatively poor efficacy. Other compounds with a hydroquinone core structure have been described in the patent literature, for example, U.S. Pat. No. 5,449,518 refers to 2,5-dihydroxyphenyl carboxylic acid derivatives, and European Patent Application EP 341,664A1 and PCT International Publication WO 99/15148 refer to certain resorcinol derivatives as tyrosinase inhibitors.

A variety of additional agents have been applied to the skin to lighten the skin. Such agents include but are not limited to kojic acid, licorice and its derivatives, ascorbic acid and its derivatives, arbutin, bearberry, *Glycyrrhiza glabra* and its derivatives, *Chlorella vulgaris* extract, perilla extract, and coconut fruit extract. *Perilla* extract is disclosed as a whitening agent in U.S. Pat. No. 5,980,904 and Japanese Publications Nos. 07-025742, 07-187989, 10-265322, 2001-163759 and 2001-181173. Coconut fruit extract is disclosed as a whitening agent in Japanese Patent No. 2896815 B2.

Resorcinol (1,3-benzenediol) derivatives have been used to provide cosmetic benefits to skin and hair. 4-Substituted resorcinol derivatives have been used for skin lightening; see, for example, U.S. Pat. Nos. 4,959,393, 6,132,740, 6,504,037, U.S. Patent Application Publication No. 2008/0131382, and Japanese Published Patent Application Nos. JP 2001-01 0925 and JP 2000-327557. Resorcinol derivative dimers which are inhibitors of tyrosinase are disclosed in U.S. Pat. No. 5,399,785. Resorcinol-type skin lightening agents, which can be synthesized using coumarin as starting material, are disclosed in U.S. Patent Application Publication No. 2004/0042983. However, some of these compounds can be difficult to formulate, or may cause skin irritation.

It would be desirable to have a safe and non-toxic composition for the treatment or prevention of the pigmentation disorders. The compounds and compositions comprising resorcinols described herein fill this need.

BRIEF DESCRIPTION

Provided herein are methods for reducing or improving the appearance of visible discontinuities in skin associated with age-related damage, or damage resulting from harmful ultraviolet radiation, such as that contained in sunlight, pollution and other environmental insults, stress, or fatigue. Also provided herein are methods for reducing the appearance of coloration due to pigmentation disorders. Also provided are compositions and methods of improving skin appearance by alleviating skin discoloration associated with age and reducing the appearance of coloration due to pigmentation disorders simultaneously. Also provided are resorcinol derivatives for reducing or preventing the appearance of skin pigmentation and the skin problems arising with age, and compositions comprising such resorcinol derivatives, such pharmaceutically acceptable compositions, including topical pharmaceutically acceptable compositions.

Also provided are methods for reducing or improving the appearance of pigmentation or discoloration in skin. Also provided are methods of reducing age spots, liver spots, and other age-related pigmentation disorders, and method of treating pigmentation disorders such as vitiligo and melasma. The methods comprise applying a therapeutically or cosmetically effective amount of the compounds to the skin in an amount sufficient to reduce or improve the appearance of pigmentation or discoloration in skin, or in an amount sufficient to reduce age spots, liver spots, or other age-related pigmentation disorders, or in an amount sufficient to treat a pigmentation disorder, such as vitiligo and melasma. Also provided are compounds for use in reducing or improving the appearance of pigmentation or discoloration in skin, or for use in reducing age spots, liver spots, or other age-related pigmentation disorders, or for use in treating a pigmentation disorder, such as vitiligo and melasma.

The resorcinol derivatives provided herein, which are defined below and used in the various methods provided herein, are useful in the treatment or prevention of one or more dermatological conditions as desired by the subject being treated, such as for medicinal or cosmetic purposes, such as to prevent, lighten, reduce or treat the signs or appearance of undesired pigmentation of skin affected by the one or more conditions.

Provided herein is a cosmetic or dermatological composition comprising one or more resorcinols of formula I:

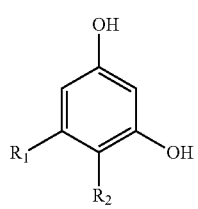

(I)

wherein $R^1$ and $R^2$ are independently alkyl, alkenyl, cycloalkyl, heterocycloalkyl, aryl, heteroaryl, or halo, each of which alkyl, alkenyl, cycloalkyl, heterocycloalkyl, aryl, or heteroaryl is optionally substituted with —OH, —OR$^3$, —NR$^3$R$^4$, —C(O)OR$^3$, —C(O)NR$^3$R$^4$, or halo; and $R^3$ and $R^4$ are independently hydrogen, alkyl, alkenyl, cycloalkyl, heterocycloalkyl, cycloalkyl-alkyl, heterocycloalkyl-alkyl, arylalkyl, heteroarylalkyl, aryl, or heteroaryl; or a pharmaceutically acceptable salt thereof. Also provided are mixtures of two or more compounds of formula I. In some variations, $R^1$ is alkyl or halo, and $R^2$ is alkyl or cycloalkyl. In some variations, $R^1$ is alkyl, such as methyl. In some variations, $R^1$ is haloalkyl, perhaloalkyl, fluoroalkyl, or perfluoroalkyl, such as trifluoromethyl. In some variations, $R^1$ is halo, such as fluoro, chloro, bromo, or iodo. In some variations, $R^1$ is fluoro or chloro. In some variations, $R^2$ is alkyl, such as ethyl or hexyl. In some variations, $R^2$ is cycloalkyl, such as cyclohexyl.

In some variations, $R^1$ is $(C_1$-$C_6)$-alkyl, $(C_2$-$C_6)$-alkenyl, $(C_3$-$C_8)$-cycloalkyl, $(C_3$-$C_8)$-heterocycloalkyl, $(C_6$-$C_{12})$-aryl, $(C_3$-$C_{12})$-heteroaryl, or halo, each of which $(C_1$-$C_6)$-alkyl, $(C_2$-$C_6)$-alkenyl, $(C_3$-$C_8)$-cycloalkyl, $(C_3$-$C_8)$-heterocycloalkyl, $(C_6$-$C_{12})$-aryl, or $(C_3$-$C_{12})$-heteroaryl is optionally substituted with one, two, or three substituents selected from the group consisting of —OH, —OR$^3$, —NR$^3$R$^4$, —C(O)OR$^3$, —C(O)NR$^3$R$^4$, or halo; and $R^2$ is $(C_1$-$C_6)$-alkyl, $(C_2$-$C_6)$-alkenyl, $(C_3$-$C_8)$-cycloalkyl, $(C_3$-$C_8)$-heterocycloalkyl, $(C_6$-$C_{12})$-aryl, $(C_3$-$C_{12})$-heteroaryl, or halo, each of which $(C_1$-$C_6)$-alkyl, $(C_2$-$C_6)$-alkenyl, $(C_3$-$C_8)$-cycloalkyl, $(C_3$-$C_8)$-heterocycloalkyl, $(C_6$-$C_{12})$-aryl, or $(C_3$-$C_{12})$-heteroaryl is optionally substituted with one, two, or three substituents selected from the group consisting of —OH, —OR$^3$, —NR$^3$R$^4$, —C(O)OR$^3$, —C(O)NR$^3$R$^4$, or halo.

In some variations, $R^1$ is $(C_1$-$C_6)$-alkyl, $(C_2$-$C_6)$-alkenyl, $(C_3$-$C_8)$-cycloalkyl, $(C_3$-$C_8)$-heterocycloalkyl, $(C_6$-$C_{12})$-aryl, $(C_3$-$C_{12})$-heteroaryl, or halo, each of which $(C_1$-$C_6)$-alkyl, $(C_2$-$C_6)$-alkenyl, $(C_3$-$C_8)$-cycloalkyl, $(C_3$-$C_8)$-heterocycloalkyl, $(C_6$-$C_{12})$-aryl, or $(C_3$-$C_{12})$-heteroaryl is optionally substituted with one, two, or three substituents selected from the group consisting of —OH, —OR$^3$, —NR$^3$R$^4$, —C(O)OR$^3$, —C(O)NR$^3$R$^4$, or halo; and $R^2$ is cycloalkyl, such as $(C_3$-$C_8)$-cycloalkyl, such as cyclohexyl.

In some variations, $R^3$ and $R^4$ are independently hydrogen, $(C_1$-$C_6)$-alkyl, $(C_2$-$C_6)$-alkenyl, $(C_3$-$C_8)$-cycloalkyl, $(C_3$-$C_8)$-heterocycloalkyl, $(C_3$-$C_8)$-cyclo alkyl-$(C_1$-$C_6)$-alkyl, $(C_3$-$C_8)$-heterocycloalkyl-$(C_1$-$C_6)$-alkyl, $(C_6$-$C_{12})$-aryl-$(C_1$-$C_6)$-alkyl, $(C_3$-$C_{12})$-heteroaryl-$(C_1$-$C_6)$-alkyl, $(C_6$-$C_{12})$-aryl, or $(C_3$-$C_{12})$-heteroaryl.

In some variations, $R^1$ is $(C_1$-$C_6)$-alkyl, $(C_2$-$C_6)$-alkenyl, $(C_3$-$C_8)$-cycloalkyl, or halo, and $R^2$ is $(C_1$-$C_6)$-alkyl, $(C_2$-$C_6)$-alkenyl, or $(C_3$-$C_8)$-cycloalkyl.

In some variations, $R^1$ is $(C_1$-$C_6)$-alkyl or halo, and $R^2$ is $(C_1$-$C_6)$-alkyl or $(C_3$-$C_8)$-cycloalkyl.

In some variations, $R^1$ is methyl, fluoro, or trifluoromethyl, and $R^2$ is ethyl, hexyl, or cyclohexyl.

In particular variations, the cosmetic or dermatological composition contains one or more of the following compounds:

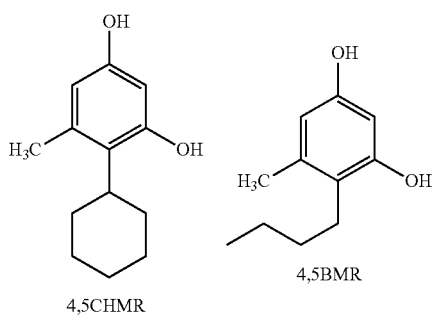
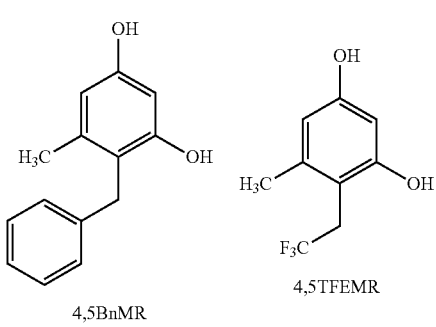
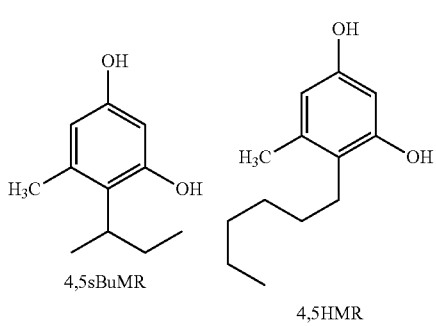
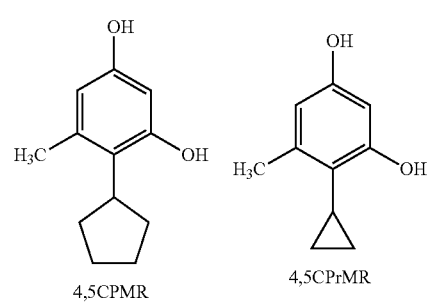
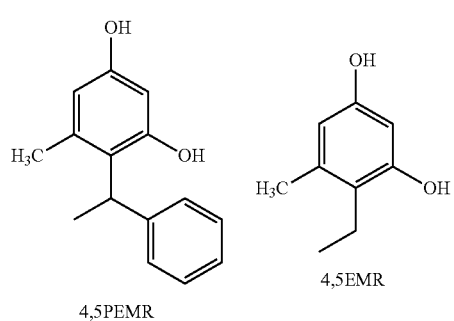
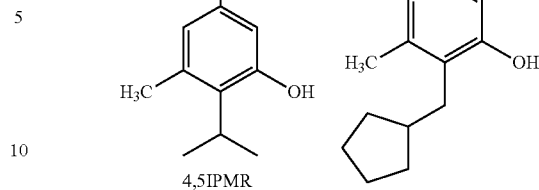
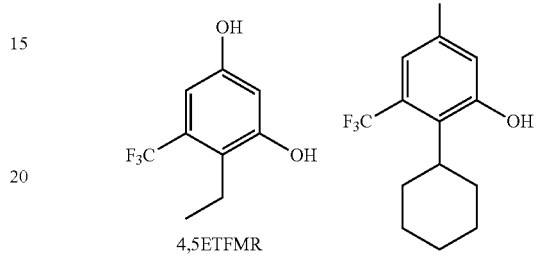
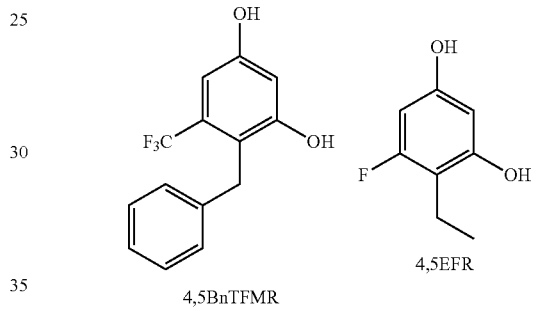
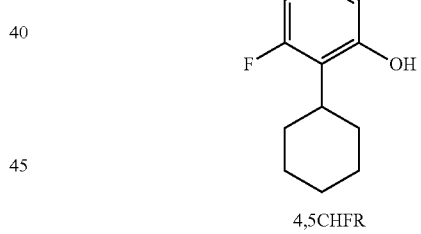

or a pharmaceutically acceptable salt thereof.

In some variations, the cosmetic and dermatological compositions comprising one or more compounds of formula I may be used for the prophylaxis and treatment of cosmetic and dermatological skin changes in a subject in need thereof, such as undesirable skin pigmentation or changes in skin pigmentation or skin tone, which is achieved by administering an effective amount of one or more of the compositions to the subject. In some variations, the skin changes are produced by oxidative or degenerative processes.

In some variations, the cosmetic and dermatological compositions comprising one or more compounds of formula I may be used for preventing, lightening or reducing visible signs from aging in a subject, which is achieved by administering an effective amount of one or more of the compositions to the subject. In some variations, the cosmetic and dermatological compositions comprising one or more compounds of formula I may be used in a subject for reducing the appearance of visible, tactile, and/or coloration discontinuities in skin associated with aging, age-related damage, or damage resulting from harmful factors, such as those contained in sunlight, harmful ultraviolet radiation, pollution and other environmental insults, stress, or fatigue, which is achieved by administering an effective amount of one or more of the compositions to the subject.

In some variations, the cosmetic and dermatological compositions comprising one or more compounds of formula I may be used in a subject for the prophylaxis or treatment of dermatological conditions comprising unevenness or pigmentation of the skin, which is achieved by administering an effective amount of one or more of the compositions to the subject.

In some variations, the cosmetic and dermatological compositions comprising one or more compounds of formula I may be used in a subject for preventing, lightening or reducing the appearance of visible and/or tactile discontinuities of the skin, such as mottling, which is achieved by administering an effective amount of one or more of the compositions to the subject.

In some variations, the cosmetic and dermatological compositions comprising one or more compounds of formula I may be used in a subject for preventing, lightening or reducing the appearance of visible discontinuities of the skin resulting from the aging processes, which is achieved by administering an effective amount of one or more of the compositions to the subject.

In some variations, the cosmetic and dermatological compositions comprising one or more compounds of formula I may be used in a subject for preventing, lightening or reducing the appearance of visible discontinuities of the skin such as pigmentation, age spots, vitiligo and melasma, which is achieved by administering an effective amount of one or more of the compositions to the subject.

In some variations, the cosmetic and dermatological compositions comprising one or more compounds of formula I may be used in a subject for preventing, lightening or reducing the appearance of visible discontinuities of the skin such as coloration, discoloration, or pigmentation resulting from stress, fatigue, or extrinsic insults such as harmful factors contained in sunlight, harmful ultraviolet radiation, pollution and other environmental insults, which is achieved by administering an effective amount of one or more of the compositions to the subject.

In some variations, the cosmetic and dermatological compositions comprising one or more compounds of formula I may be used for preventing, lightening or reducing the appearance of dark circles, dark spots and uneven skin tone, which is achieved by administering an effective amount of one or more of the compositions to the subject.

In another variation, the cosmetic and dermatological compositions comprising one or more compounds of formula I may be used for reducing the appearance of visible discontinuities in skin associated with inflammation, which is achieved by administering an effective amount of one or more of the compositions to the subject. The visible discontinuities may be caused by post-inflammatory hypopigmentation or hyperpigmentation. The inflammation may be due to various causes. The inflammation may be caused by rosacea. The inflammation may be caused by diaper rash. The inflammation may be caused by acne. The inflammation may be caused by dermatitis such as atopic dermatitis, contact dermatitis, or seborrheic dermatitis. The inflammation may be caused by poison ivy or poison oak. The inflammation may be caused by erythema. The inflammation may be caused by psoriasis.

Also provided herein is a cosmetic composition comprising a cosmetically acceptable or dermatologically acceptable carrier in combination with any one or more of the compounds of formula I. The carrier can be formulated for topical use.

Also provided herein is a cosmetic composition comprising a pharmaceutically acceptable carrier in combination with any one or more of the compounds of formula I.

In one variation, provided herein are methods for reducing the appearance of visible discontinuities in skin, such as coloration, discoloration, or pigmentation discontinuities, with a composition comprising one or more compounds of formula I, wherein the composition is included in a topical formulation, comprising administering an effective amount of the composition to a subject.

In one variation, provided herein are methods for reducing the appearance of visible discontinuities in skin such as coloration, discoloration, or pigmentation discontinuities, with a composition comprising one or more compounds of formula I, wherein the composition is included in a topical pharmaceutical formulation, comprising administering an effective amount of the one or more compounds of formula I to a subject. In further embodiments, the administration is topical or dermatological administration. The composition can comprise pharmaceutically and/or dermatologically acceptable carriers and vehicles.

In one variation, provided herein are methods for reducing the appearance of visible discontinuities in skin such as coloration, discoloration, or pigmentation discontinuities, with a composition comprising one or more compounds of formula I, wherein the composition is formulated for transdermal administration, comprising administering an effective amount of the one or more compounds of formula I to the skin of a subject. The composition can comprise pharmaceutically and/or dermatologically acceptable carriers and vehicles.

Also provided herein is a method of lightening skin of a subject while providing reduction or treatment or prevention of signs of skin aging, comprising administering to said subject an amount of one or more compounds of formula I effective for even-toning, skin-lightening or pigmentation-reducing. In further embodiments, the administration is topical or dermatological administration. In a particular variation, provided herein is a method of lightening skin of a subject in need of said treatment while providing reduction or treatment or prevention of signs of skin aging, comprising administering to said subject an amount of a composition comprising a compound of formula I effective to even-tone the skin, lighten the skin, or reduce pigmentation in the skin. In further embodiments, the administration is topical or dermatological administration. The composition can comprise pharmaceutically and/or dermatologically acceptable carriers and vehicles.

Further provided is a method of improving the appearance of skin of a subject, comprising administering to said subject an amount of a composition comprising a compound of formula I effective to reduce pigmentation. In further embodiments, the administration is topical or dermatological administration. In a particular variation, provided herein is a method of reducing or preventing the appearance of pigmentation in a subject in need of said treatment, comprising administering to said subject an amount of a composition comprising a compound of formula I effective to reduce the appearance of pigmentation in a subject or to prevent the appearance of pigmentation in a subject. The composition can comprise pharmaceutically and/or dermatologically acceptable carriers and vehicles. In some variations, provided is a method of treating pigmentation or reducing the appearance of pigmentation or prophylaxis against the appearance of pigmentation, by administering an effective amount of a composition comprising a compound of formula I. In some variations the subject has a pigmentation disorder selected from age spots, vitiligo and melasma.

In another variation, provided herein is a method of treating or regulating a skin condition characterized by oxidative stress comprising administering to a subject exhibiting said skin condition a composition comprising one or more compounds of formula I. The composition can comprise pharmaceutically and/or dermatologically acceptable carriers and vehicles. In further embodiments, the administration is topical or dermatological administration.

In another variation, provided herein is a method of regulating and/or preventing visible signs of skin aging comprising administering to a subject exhibiting skin damage due to aging, a composition comprising one or more compounds of formula I. The composition can comprise pharmaceutically and/or dermatologically acceptable carriers and vehicles. In further embodiments, the administration is topical or dermatological administration.

In another variation, provided herein is a method of regulating and/or preventing visible signs of skin damage due to extrinsic factors comprising administering to a subject exhibiting skin damage a composition comprising an effective amount of one or more compounds of formula I. The composition can comprise pharmaceutically and/or dermatologically acceptable carriers and vehicles. In further embodiments, the administration is topical or dermatological administration. The extrinsic factors can include, but are not limited to, diaper rash, erythema, UV radiation damage, sunburn, photoaging, contact dermatitis, and combinations thereof.

Also provided herein is a method of reducing the appearance of pigmentation and aging processes in the skin of a subject, comprising administering to said subject an amount of a composition comprising one or more compounds of formula I effective to reduce the appearance of pigmentation, or to prevent the appearance of pigmentation, in combination with another therapeutic agent. In one variation, provided herein is a method of reducing the appearance of pigmentation, or preventing the appearance of pigmentation, in the skin of a subject, comprising administering to said subject an effective amount of a composition comprising one or more compounds of formula I in combination with an antioxidant. In one variation, provided herein is a method of reducing the appearance of pigmentation and aging processes, or preventing the appearance of pigmentation and aging processes, in a subject in need of said treatment, comprising administering to said subject an effective amount of a composition comprising one or more compounds of formula I in combination with ascorbic acid or derivatives thereof. In another variation, provided herein is a method of reducing the appearance of pigmentation and aging processes, or preventing the appearance of pigmentation and aging processes, in a subject in need of said treatment, comprising administering to said subject an effective amount of a composition comprising one or more compounds of formula I in combination with alpha-tocopherol or any mixture of tocopherols or derivatives thereof. In another variation, provided herein is a method of reducing the appearance of pigmentation and aging processes, or preventing the appearance of pigmentation and aging processes, in a subject in need of said treatment, comprising administering to said subject an effective amount of a composition comprising one or more compounds of formula I in combination with alpha-tocotrienol or any mixture of tocotrienols or derivatives thereof. In another variation, provided herein is a method of reducing the appearance of pigmentation and aging processes, or preventing the appearance of pigmentation and aging processes, in a subject in need of said treatment, comprising administering to said subject an effective amount of a composition comprising one or more compounds of formula I in combination with any mixture of tocopherols and tocotrienols or derivatives thereof. In yet another variation, provided herein is a method of reducing the appearance of pigmentation and aging processes, or preventing the appearance of pigmentation and aging processes, in a subject in need of said treatment, comprising administering to said subject an effective amount of a composition comprising one or more compounds of formula I in combination with ascorbic acid and alpha-tocopherol or derivatives thereof. In other variations, provided herein is a method of reducing the appearance of pigmentation and aging processes, or preventing the appearance of pigmentation and aging processes, in a subject in need of said treatment, comprising administering to said subject an effective amount of a composition comprising one or more compounds of formula I in combination with retinoids or an exfoliating agent. When administered in combination, the therapeutic agents can be formulated as separate compositions that are given at the same time or different times, or the therapeutic agents can be given as a single composition. The composition can also comprise pharmaceutically and/or dermatologically acceptable carriers and vehicles. In any of the foregoing embodiments, the administration can be topical or dermatological administration.

Also provided herein is a product comprising instructions directing a user to apply a composition including a skin care composition comprising one or more compounds of formula I. The composition can comprise pharmaceutically and/or dermatologically acceptable carriers and vehicles.

Also provided herein is a kit, comprising a container comprising one or more specific compounds or dermatological compositions described herein that lighten skin pigmentation. The kit may further comprise printed instructions as a label or a package insert directing the use of the enclosed compound or composition to lighten skin pigmentation.

Also provided for herein is the use of a composition of any of the foregoing variations in the manufacture of a cosmetic or dermatological composition for treating a mammalian subject, such as a human, having a dermatologic condition, where the treatment is to prevent, reduce or treat signs of skin aging or skin pigmentation, or to reduce the appearance of skin aging or skin pigmentation.

For all compositions described herein, and all methods using a composition described herein, the compositions can either comprise the listed components or steps, or can "consist essentially of" the listed components or steps. When a composition is described as "consisting essentially of" the listed components, the composition contains the components listed, and may contain other components which do not substantially affect the skin or the skin condition being treated, but do not contain any other components which substantially affect the skin or the skin condition being treated other than those components expressly listed; or, if the composition does contain extra components other than those listed which substantially affect the skin or the skin condition being treated, the composition does not contain a sufficient concentration or amount of the extra components to substantially affect the skin or the skin condition being treated. When a method is described as "consisting essentially of" the listed steps, the method contains the steps listed, and may contain other steps that do not substantially affect the skin or the skin condition being treated, but the method does not contain any other steps which substantially affect the skin or the skin condition being treated other than those steps expressly listed.

DETAILED DESCRIPTION

Definitions

As used herein, a "subject" or "patient" is a mammal, particularly a human. It is understood that use "in" a subject or patient can comprise use "on" a subject or patient as well; that is, use "in" a subject or patient can comprise either internal use, external use, or both, according to the context of the use.

As used herein, the terms "even-toning", "whitening", "lightening" and "depigmentation" agent are used interchangeably throughout this document. For purposes of skin lightening, topical application of skin lightening agent should have a lightening effect on only the area to be treated, preferably produce no or minimal irritation, preferably produce no or minimal post-inflammatory secondary pigmentation, and preferably not cause an allergic reaction. In addition, the skin lightening should be effective for normal cutaneous pigmentation and its excesses, including, but not limited to, lentigo senilis, chloasma, cicatrical brown spots, and hyperpigmentation after use of photosensitizing products. Preferably, the skin lightening should be effective while simultaneously providing anti-aging skin benefits.

As used herein, a "skin-lightening or pigmentation reducing amount of a compound of formula I" means an amount or concentration of the compound capable of detectably lightening skin or reducing pigmentation in a subject, such as a human, as determined by any standard assay. The active compound is typically administered in a dermatological or pharmaceutical composition for a standard course of treatment that produces the desired result of skin depigmentation.

As used herein, "administering to skin in need of such treatment" means contacting (e.g., by use of the hands or an applicator such as, but not limited to, a wipe, tube, roller, spray, or patch) the area of skin in need such treatment or an area of skin proximate to the area of skin in need of such treatment.

As used herein, "composition" means a composition suitable for topical administration to the skin.

As used herein, the term "cosmetics" includes make-up, foundation, and skin care products. The term "make-up" refers to products that leave color on the face, including foundations, blacks and browns, e.g., mascara, concealers, eye liners, brow colors, eye shadows, blushers, lip colors, and so forth. The term "foundation" refers to liquid, creme, mousse, pancake, compact, concealer, or like products that even out the overall coloring of the skin. Foundation is typically manufactured to work better over moisturized and/or oiled skin. The term "skin care products" refers to products used to treat or otherwise care for, moisturize, improve, or clean the skin. Products contemplated by the phrase "skin care products" include, but are not limited to, adhesives, bandages, anhydrous occlusive moisturizers, antiperspirants, facial wash cleaners, cold cream, deodorants, soaps, occlusive drug delivery patches, powders, tissues, wipes, solid emulsion compact, anhydrous hair conditioners, medicated shampoos, scalp treatments and the like.

As used herein, the term "cosmetically-acceptable" or "dermatologically-acceptable" means that the compositions or components thereof so-described are suitable for use in contact with skin, particularly human skin, without undue toxicity, incompatibility, instability, irritation, or allergic response.

As used herein, the term "cosmetically acceptable carrier", "cosmetically acceptable excipient", "dermatologically acceptable carrier" or "dermatologically acceptable excipient" includes any and all solvents, dispersion media, coatings, antibacterial and antifungal agents, isotonic and absorption delaying agents and the like, that are cosmetically acceptable or dermatologically acceptable. The use of such media and agents for cosmetically active substances is well known in the art. Except insofar as any conventional media or agent is incompatible with the active ingredient, its use in the cosmetic compositions is contemplated. Supplementary active ingredients can also be incorporated into the compositions. Dermatologically acceptable carriers are suitable for topical application to the skin, have good aesthetic properties, are compatible with the active agents described herein and any other components, and cause minimal or no safety or toxicity concerns. A safe and effective amount of carrier is from about 50% to about 99.99% or about 50% to about 99%, preferably from about 80% to about 99.9% or about 75% to about 99%, more preferably from about 90% to about 98%, and most preferably from about 90% to about 95% or about 85% to about 95% of the composition. The percentages are preferably percent by weight.

As used herein, the term "effective amount" refers to that amount of a compound described herein that is sufficient to effect treatment, as defined below, when administered to a subject in need of such treatment. The effective amount will vary depending upon the subject and skin condition or disease condition being treated and the like, all of which can readily be determined by one of ordinary skill in the art.

As used herein, "regulating a skin condition" includes regulating the appearance of a skin condition, including visible discontinuities in skin such as, but not limited to, coloration, discoloration, and unwanted pigmentation. Regulating a skin condition includes even-toning the skin and reducing pigmentation.

As used herein, "signs of skin aging" include, but are not limited to, all outward manifestations of skin aging which are visibly perceptible due to changes in skin pigmentation, skin coloration, or skin discoloration. Such signs may be induced or caused by intrinsic factors or extrinsic factors, e.g., chronological aging and/or environmental damage (e.g., sunlight; UV; smoke, including cigarette, cigar or other tobacco product smoke; ozone; pollutants; stress; etc.). These signs include, but are not limited to, blotching (e.g., uneven red coloration due to, e.g., rosacea), sallowness (pale color), discoloration caused by telangiectasia or spider vessels; melanin-related hyperpigmented (or unevenly pigmented) skin regions such as age spots (liver spots, brown spots) and freckles; post-inflammatory hyperpigmentation or hypopigmentation such as that which occurs following an inflammatory event (e.g., as an acne lesion, in-grown hair, insect/spider bite or sting, scratch, cut, wound, abrasion, and the like); and tissue responses to insult such as itch or pruritus.

As used herein, the terms "skin condition", "dermatologic condition", and "dermatological condition" are used interchangeably.

As used herein, the term "sunscreen" may include, but is not limited to, organic or inorganic sunscreens, such as methoxycinnamate, oxybenzone, avobenzone, and the like; sun blocks such as titanium oxide and zinc oxide; and skin protectants; or mixtures thereof.

As used herein, the term "topical application" means to apply or spread the compositions described herein onto the surface of the skin.

As used herein, the terms "treat" and "treating", and the like refer to reversing, alleviating, or inhibiting the progress of, the disorder or condition to which such term applies, or one or more symptoms of such disorder or condition. The term "treatment", as used herein, refers to the act of treating, as "treating" is defined immediately above. The term "treatment" or "treating" includes the reduction in appearance of skin imperfections irrelevant of the mechanism of action. One of ordinary skill in the art will appreciate that the endpoint of treatment chosen in a particular case will vary according to the disease, condition, or disorder being treated, the outcome desired by the patient, subject, or treating physician, and other factors. Where the composition is being used to lighten skin color such as, for example, to reverse hyperpigmentation caused by, for example, diseases such as melasma or age spots, any one of a number of endpoints can be chosen. For example, endpoints can be defined subjectively such as, for example, when the subject is simply "satisfied" with the results of the treatment. For pharmacological compositions, the endpoint can be determined by the patient's, subject's, or the treating physician's, satisfaction with the results of the treatment. Alternatively, endpoints can be defined objectively. For example, the patient's or subject's skin in the treated area can be compared to a color chart. Treatment is terminated when the color of the skin in the treated area is similar in appearance to a color on the chart. Alternatively, the reflectance of the treated skin can be measured, and treatment can be terminated when the treated skin attains a specified reflectance. Alternatively, the melanin content of the treated skin can be measured. Treatment can be terminated when the melanin content of the treated skin reaches a specified value. Melanin content can be determined in any way known to the art, including by histological methods, with or without enhancement by stains for melanin.

As used herein, "alkyl" is intended to embrace a saturated linear or branched hydrocarbon chain having the number of carbon atoms specified. In one embodiment, alkyl groups can have 1 to 12 carbon atoms. "Alkylene" is intended to embrace a divalent saturated linear or branched hydrocarbon chain having the number of carbon atoms specified. In one embodiment, alkylene groups can have 1 to 12 carbon atoms.

As used herein, "cycloalkyl" is intended to embrace a saturated cyclic hydrocarbon chain having the number of carbon atoms specified. In one embodiment, cycloalkyl groups can have 3 to 12 carbon atoms.

As used herein, "alkenyl" is intended to embrace a linear or branched hydrocarbon chain having at least one carbon-carbon double bond. In one embodiment, alkenyl groups can have 2 to 12 carbon atoms. "Alkenylene" is intended to embrace a divalent linear or branched hydrocarbon chain having at least one carbon-carbon double bond, and having the number of carbon atoms specified. In one embodiment, alkenylene groups can have 2 to 12 carbon atoms.

As used herein, "haloalkyl" indicates an alkyl group where at least one hydrogen of the alkyl group has been replaced with a halogen substituent, that is, a fluorine (F), chlorine (Cl), bromine (Br), or iodine (I) substituent. "Perhaloalkyl" indicates an alkyl group where all available valences have been substituted with halogen. For example, "perhaloethyl" can refer to —$CCl_2CF_3$, —$CF_2CBr_3$, or —$CCl_2CCl_3$.

As used herein, "fluoroalkyl" indicates an alkyl group where at least one hydrogen of the alkyl group has been replaced with a fluorine substituent. "Perfluoroalkyl" indicates an alkyl group where all available valences have been substituted with fluorine. For example, "perfluoroethyl" refers to —$CF_2CF_3$.

As used herein, "chloroalkyl" indicates an alkyl group where at least one hydrogen of the alkyl group has been replaced with a chlorine substituent. "Perchloroalkyl" indicates an alkyl group where all available valences have been substituted with chlorine. For example, "perchloroethyl" refers to —$CCl_2CCl_3$.

As used herein, "aryl" is defined as an optionally substituted aromatic ring system, such as phenyl or naphthyl. Aryl groups include monocyclic aromatic rings and polycyclic aromatic ring systems containing the number of carbon atoms specified. In one embodiment, aryl groups can contain six to twenty carbon atoms. In other embodiments, aryl groups can contain six to twelve carbon atoms, or six to ten carbon atoms. In other embodiments, aryl groups can be unsubstituted. In other embodiments, aryl groups can be substituted.

As used herein, "heterocycloalkyl" is intended to embrace an optionally substituted cyclic hydrocarbon chain having the number of carbon atoms specified and one or more heteroatoms (such as one to three heteroatoms, such as oxygen, nitrogen, sulfur, and phosphorus). In one embodiment, heterocycloalkyl groups can have 3 to 12 carbon atoms and 1 to 3 heteroatoms. Examples of heterocycloalkyl groups include, but are not limited to, tetrahydrofuranyl, piperidinyl, and piperazinyl. In some embodiments, heterocycloalkyl groups can be unsubstituted. In other embodiments, heterocycloalkyl groups can be substituted.

As used herein, "heteroaryl" is defined as an optionally substituted aromatic ring system which contains the number of carbon atoms specified, and one or more heteroatoms (such as one to three heteroatoms), where heteroatoms include, but are not limited to, oxygen, nitrogen, sulfur, and phosphorus. In some embodiments, heteroaryl groups can contain three to twelve carbon atoms and one to three heteroatoms, or six to ten carbon atoms and one to three heteroatoms. In some embodiments, heteroaryl groups can be unsubstituted. In other embodiments, heteroaryl groups can be substituted. Examples of heteroaryl groups include, but are not limited to, imidazolyl, pyrrolyl, and pyridinyl.

As used herein, the term "tocopherols or tocotrienols" encompasses a family of molecules characterized by a 6-chromanol ring structure and a side chain at the 2-position. Tocopherols possess a 4',8',12'-trimethyltridecyl phytol side chain, while tocotrienols possess an unsaturated phytol side chain. As used herein, the term tocopherol or tocotrienols means alpha-, beta-, gamma- or delta-, epsilon- and zeta-tocopherol or tocotrienols (see The Merck Index (1996), Merck & Co., Whitehouse Station, N.J. 1620-1621 and 1712, and references cited therein), as well as Vitamin E. The term tocopherol also includes cosmetically acceptable esters, for example tocopherol acetate, tocopherol lineate, or tocopherol stearate. The term tocopherol also includes mixtures of tocopherols, tocotrienols and/or stereoisomers as well as enriched compositions comprising at least 50% of any tocopherol or tocotrienol. The tocopherols and tocotrienols can be of natural or synthetic origin.

As used herein, the term "retinoids" means retinol, retinal, esters of retinol, retinyl palmitate, retinyl linoleate, retinoic acid, or retinoic acid esters, as well as synthetic or natural Vitamin A. The term "retinol" includes the following isomers of retinol: all-trans-retinol, 13-cis-retinol, 11-cis-retinol, 9-cis-retinol, 3,4-didehydro-retinol. A retinyl ester is an ester of retinol. Suitable retinyl esters are $C_1$-$C_{30}$ esters of retinol, preferably $C_2$-$C_{20}$ esters, and most preferably $C_2$, $C_3$, and $C_{16}$ esters. Some esters may be selected from retinyl palmitate, retinyl acetate, retinyl propionate, and retinyl linoleate. Retinoyl ester is an ester of retinoic acid with an alcohol. Suitable retinoyl esters include $C_1$-$C_{30}$ alcohol esters of retinoic acid, preferably $C_2$-$C_{20}$ esters and most preferably $C_2$-$C_3$ and $C_{16}$ esters. Some retinoyl esters comprise the linoleyl alcohol ester of retinoic acid, the hexanedecanol ester of retinoic acid, the oleic alcohol ester of retinoic acid, retinoyl ascorbate, and the linolenyl alcohol ester of retinoic acid.

While the compounds described herein can occur and can be used as the neutral (non-salt) compound, the description is intended to embrace all salts of the compounds described herein, as well as methods of using such salts of the compounds. In one embodiment, the salts of the compounds comprise pharmaceutically acceptable salts and/or dermatologically acceptable salts. Pharmaceutically acceptable salts are those salts which can be administered as drugs or pharmaceuticals to humans and/or animals and which, upon administration, retain at least some of the biological activity of the free compound (neutral compound or non-salt compound). Dermatologically acceptable salts are those salts which can be applied as drugs or pharmaceuticals to the skin of humans and/or animals and which, upon application, retain at least some of the biological activity of the free compound (neutral compound or non-salt compound). The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, can also be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N-dibenzylethylenediamine, and triethylamine salts. Salts of acidic compounds with amino acids, such as lysine salts, can also be prepared. Other pharmaceutically acceptable salts are described in Bighley, "Salt Forms of Drugs," Encyclopedia of Pharmaceutical Technology vol. 13 pp 453-499 (1996) (Swarbrick, Boylan, eds.), and Berge, "Pharmaceutical Salts," J. Pharm. Sci. 66:1 (1977).

The invention also includes, if chemically possible, all stereoisomers of the compounds, including diastereomers and enantiomers. The invention also includes mixtures of possible stereoisomers in any ratio, including, but not limited to, racemic mixtures. Unless stereochemistry is explicitly indicated in a structure, the structure is intended to embrace all possible stereoisomers of the compound depicted. If stereochemistry is explicitly indicated for one portion or portions of a molecule, but not for another portion or portions of a molecule, the structure is intended to embrace all possible stereoisomers for the portion or portions where stereochemistry is not explicitly indicated.

The compounds can be administered in prodrug form. Prodrugs are derivatives of the compounds, which are themselves relatively inactive but which convert into the active compound when introduced into the subject in which they are used by a chemical or biological process in vivo, such as an enzymatic conversion. Suitable prodrug formulations include, but are not limited to, peptide conjugates of the compounds of the invention and esters of compounds of the inventions. Further discussion of suitable prodrugs is provided in H. Bundgaard, Design of Prodrugs, New York: Elsevier, 1985; in R. Silverman, The Organic Chemistry of Drug Design and Drug Action, Boston: Elsevier, 2004; in R. L. Juliano (ed.), Biological Approaches to the Controlled Delivery of Drugs (Annals of the New York Academy of Sciences, v. 507), New York: New York Academy of Sciences, 1987; and in E. B. Roche (ed.), Design of Biopharmaceutical Properties Through Prodrugs and Analogs (Symposium sponsored by Medicinal Chemistry Section, APhA Academy of Pharmaceutical Sciences, November 1976 national meeting, Orlando, Fla.), Washington: The Academy, 1977.

The description of compounds herein also includes all isotopologues, for example, partially deuterated or perdeuterated analogs of all compounds herein.

Methods

Any of the compounds described herein can be mixed as cosmetics, cosmeceuticals, quasi-drugs (where applicable), or pharmaceutical drugs. The compounds can appropriately be mixed with other components. Examples of such components include oily components such as hydrocarbons, fats and oils such as liquid paraffin, squalene, petroleum jelly such as Vaseline® (a registered trademark of Conopco Corp., Englewood Cliffs, N.J.), cetyl alcohol, isostearyl alcohol, cetyl-2-ethylhexanoate, 2-octyldodecyl alcohol, glycerin, glycerin triisostearate, nut oils, and lanolin, as well as wax, silicone, surfactants, thickeners, neutralizers, antiseptics, germicides, anti-oxidants, powder components, pigments, perfumes, ultraviolet light absorbents, drugs, metallic sealant, and pH modifiers.

Occurrences in the skin of noticeable but undesired pigmentation as a result of overproduction or underproduction of melanin or of noticeable uneven texture as a result of aging can be reduced, treated or prevented using the methods described herein. Cosmetic applications for methods described herein include the topical application of compositions containing one or more of the compounds describe herein to enhance or otherwise alter the visual appearance of skin. The cosmetic compositions described herein are also useful to provide a smoother or softer skin appearance.

The active compounds described herein can also be used in combination with skin peeling agents (including glycolic acid or trichloroacetic acid face peels) or skin exfoliating agents (including retinoids, such as retinoic acid or retinol) to lighten skin tone and prevent repigmentation. The appropriate dose regimen, the amount of each dose administered, and specific intervals between doses of the active compound will depend upon the particular active compound employed, the condition of the patient or subject being treated, and the nature and severity of the disorder or condition being treated. Preferably, the active compound is administered in an amount and at an interval that results in the desired treatment of or improvement in the disorder or condition being treated.

An active compound described herein can also be used in combination with sun screens (UVA or UVB blockers) to prevent repigmentation; to protect against sun or UV-induced skin darkening, or to enhance their skin lightening or bleaching action and to enhance their ability to reduce skin melanin. An active compound described herein can also be used in combination with any compounds that interact with retinoic acid receptors and accelerate or enhance their ability to reduce skin melanin, accelerate or enhance their skin lightening or bleaching action, or accelerate or enhance their ability to prevent the accumulation of skin melanin. An active compound described herein can also be used in combination with 4-hydroxyanisole. An active compound described herein can also be used in combination with ascorbic acid, its derivatives and ascorbic-acid based products (such as magnesium ascorbate) or other products with an anti-oxidant mechanism (such as resveratrol, tocopherols, tocotrienols and derivatives) which accelerate or enhance their ability to reduce skin melanin, or accelerate or enhance their skin bleaching action.

In some variations, the composition further comprises a soybean extract that is a blend of compounds isolated from soybean. The soybean extract may contain only a portion of the soybean (e.g., an extract of the soybean such as a lipid reduced soybean powder or filtered soymilk) or may contain the entire soybean (e.g., a ground powder of the soybean). The soybean extract may be in the form of a fluid (e.g., soymilk) or a solid (e.g., a soybean powder or soymilk powder).

One or more active compounds used in the methods described herein may be used alone or in combination with one or more other compounds known in the art. For example, any of the compounds described herein may be used in combination with a tyrosinase inhibitor or other skin-lightening, pigmentation-modifying, or skin-whitening agent, including any one or more of those agents, including compounds or extracts, described in the following patent publications: U.S. Pat. No. 4,278,656 to Nagai et al.; U.S. Pat. No. 4,959,393 to Torihara et al.; U.S. Pat. No. 5,164,182; U.S. Pat. No. 5,580,549 to Fukuda et al.; U.S. Pat. No. 5,723,109 to L'Oreal; U.S. Pat. No. 6,123,959 to Jones et al.; U.S. Pat. No. 6,132,740 to Hu; U.S. Pat. No. 6,159,482 to Tuloup et al.; U.S. Pat. No. 6,365,135 to L'Oreal; U.S. Pat. No. 6,514,538 to Shiseido Co. Ltd.; U. S. Pat. Publ, No. 2006188559 to Neis; WO 99/64025 by Fytokem Prod. Inc.; U.S. Pat. No. 6,348,204 by L'Oreal; WO 00/56702 by Pfizer Inc.; JP 5221846 by Kunimasa Tomoji; JP 7242687 by Shiseido Co. Ltd.; JP 7324023 by Itogawa H.; JP 8012552 by Shiseido Co. Ltd.; JP 8012554 by Shiseido Co. Ltd.; JP 8012557 by Shiseido Co. Ltd.; JP 8012560 by Shiseido Co. Ltd.; JP 8012561 by Shiseido Co. Ltd.; JP 8134090 by Fujisawa; JP 8277225 by Kansai Koso KK; JP 9002967 by Sanki Shoji KK; JP 9295927 by Yagi Akir; JP 10072330 by Kansai Kouso; JP 10081626 by Kamiyama KK; JP 10101543 by Kansai Kouso KK; JP 11071231 by Maruzen Pharm.; JP 11079934 by Kyodo Nyugyo; JP 11246347 by Shiseido Co. Ltd.; JP 11246344 by Shiseido Co. Ltd.; JP 2000-080023 by Kanebo Ltd.; JP 2000-095663 by Kose KK; JP 2000-159681 by Hai Tai Confectionery Co. Ltd.; JP-7206753 by Nikken Food KK; JP-59157009 by Yakurigaku Chuou KE; JP 2001019618, by Shiseido; JP 2002029959 by Shiseido; JP 2004315534 by Access Business Group Int Llc; JP 2005041821 by Shiseido; JP 2007063224 by Kobayashi Pharma; JP 2007091635 by Maruzen Pharma; JP 2008013481 by Univ. of Tokushima; KR 20040078449 by Enbioeng Co Ltd.; TW 281863 by Taiyen Biotech Co Ltd ; and CN 101102746 by Young Chung Se; among others. These patent publications are incorporated herein by reference in their entireties.

Provided herein are methods of lightening or reducing the pigmentation of skin and/or of reducing uneven texture in which an active compound described herein, and one or more of the other active ingredients, such as those referred to above, are administered together as part of the same pharmaceutical composition, as well as methods in which they are administered separately as part of an appropriate dose regimen designed to obtain the benefits of the combination therapy. The appropriate dose regimen, the amount of each dose administered, and specific intervals between doses of each active agent will depend upon the specific combination of active agents employed, the condition of the patient or subject being treated, and the nature and severity of the disorder or condition being treated. Such additional active ingredients can be administered in amounts less than or equal to those for which they are effective as single topical therapeutic agents.

An active compound will generally be administered in the form of a dermatological or cosmetic composition comprising the compound of formula I, together with a dermatologically acceptable carrier or solvent. Alternatively, an active compound can be administered in the form of a pharmaceutical composition comprising the compound of formula I, together with a pharmaceutically acceptable carrier or solvent.

In the depigmenting compositions provided herein, the concentration of the active compound is generally between 0.01% and 10%, or between about 0.01% and about 10%, for example between 0.1% and 5% or between about 0.1% and about 5%, or between 0.1% and 2%, or between about 0.1% and about 2%, or between 0.1% and 1%, or between about 0.1% and about 1%, relative to the total weight of the composition.

The compositions described herein can be applied directly to the skin. Alternatively, they can be delivered by various transdermal drug delivery systems, such as transdermal patches as known in the art. For example, for topical administration, the active ingredient can be formulated in a solution, gel, lotion, ointment, cream, suspension, paste, liniment, powder, tincture, aerosol, patch, or the like in a pharmaceutically or cosmetically acceptable form by methods known in the art. The composition can be any of a variety of forms common in the pharmaceutical or cosmetic arts for topical application to animals or humans, including solutions, lotions, sprays, creams, ointments, salves, gels, etc., as described below. Exemplary agents are those that are viscous enough to remain on the treated area, those that do not readily evaporate, and/or those that are easily removed by rinsing with water, optionally with the aid of soaps, cleansers and/or shampoos. Actual methods for preparing topical formulations are known to those skilled in the art, such as those described in Remington's Pharmaceutical Sciences, (1990); and Pharmaceutical Dosage Forms and Drug Delivery Systems, 6th ed., Williams & Wilkins (1995).

The compositions may be made into a wide variety of product types that include but are not limited to solutions, suspensions, lotions, creams, gels, toners, sticks, sprays, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, facial and skin masks, make-up such as foundations, eye liners, and eye shadows, and the like. These product types may contain several types of cosmetically-acceptable carriers including, but not limited to solutions, suspensions, emulsions such as microemulsions and nanoemulsions, gels, solids and liposomes.

The compositions can be formulated as solutions. Solutions typically include an aqueous or organic solvent, e.g., from about 50% to about 99.99% or from about 90% to about 99% of a cosmetically acceptable aqueous or organic solvent. Examples of suitable organic solvents include: propylene glycol, polyethylene glycol (200-600), polypropylene glycol (425-2025), glycerol, 1,2,4-butanetriol, sorbitol esters, 1,2,6-hexanetriol, ethanol, and mixtures thereof. One example of such solvents is a mixture of ethanol/polyethylene glycol (80/20).

A lotion can be made from such a solution. Lotions typically contain from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may contain a simple base of animal, vegetable, or synthetic oils or semi-solid hydrocarbons. An ointment may contain from about 2% to about 10% of an emollient(s) plus from about 0.1% to about 2% of a thickening agent(s). Examples of thickening agents include, but are not limited to, those set forth in the ICI Handbook (International Cosmetic Ingredient Dictionary and Handbook) pp. 1693-1697.

The compositions described herein can also be formulated as emulsions. If the carrier is an emulsion, from about 1% to about 10% (e.g., from about 2% to about 5%) of the carrier contains an emulsifier(s). Emulsifiers may be nonionic, anionic or cationic. Examples of emulsifiers include, but are not limited to, those set forth in the ICI Handbook, pp. 1673-1686.

Lotions and creams can be formulated as emulsions. Typically such lotions contain from 0.5% to about 5% of an emulsifier(s), while such creams would typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the art and are useful in compositions and methods described herein. Multiphase emulsion compositions, such as the water-in-oil-in-water type or the oil-in-water-in-oil type, are also useful in the compositions and methods describe herein. In general, such single or multiphase emulsions contain water, emollients, and emulsifiers as essential ingredients.

The compositions described herein can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contains between about 0.1% and 5%, by weight, of such gelling agents.

One or more additional agents can be added in the topical formulations in order to enhance the percutaneous absorption of the active ingredients, including, but not limited to, dimethylsulfoxide, dimethylacetamide, dimethylformamide, surfactants, azone (laurocapram), alcohol, acetone, propylene glycol and polyethylene glycol. Physical methods can also be used to enhance transdermal penetration such as iontophoresis or sonophoresis. Alternatively, or in addition, administration via liposomes can be employed.

A topically applied composition provided herein contains a pharmaceutically effective agent that has the desired effect on skin as described herein, and those ingredients as are necessary for use as a carrier, such as an emulsion, a cream, an ointment, an aqueous solution, a lotion or an aerosol. Non-limiting examples of such carriers may be found in U.S. Pat. No. 5,691,380 to Mason et al., issued Nov. 25, 1997; and U.S. Pat. No. 5,968,528 to Deckner et al., issued Oct. 19, 1999; which are incorporated herein by reference. Suitable pharmaceutical carriers are further described in Remington's Pharmaceutical Sciences, 17th ed., Mack Publishing Company, Easton, Pa. (1990).

The carrier utilized in the compositions described herein can be in a wide variety of forms. These include emulsion carriers, including, but not limited to, oil-in-water, water-in-oil, water-in-oil-in-water, and oil-in-water-in-silicone emulsions, a cream, an ointment, an aqueous solution, a lotion or an aerosol. As will be understood by the skilled artisan, a given component will distribute primarily into either the water or oil/silicone phase, depending on the water solubility/dispersibility of the component in the composition.

Dermatological formulations provided herein may typically comprise a derivative of any compound or composition described herein and optionally, a polar solvent. Solvents suitable for use in the formulations described herein include any polar solvent capable of dissolving the derivative. Suitable polar solvents may include: water; alcohols (such as ethanol, propyl alcohol, isopropyl alcohol, hexanol, and benzyl alcohol); polyols (such as propylene glycol, polypropylene glycol, butylene glycol, hexylene glycol, maltitol, sorbitol, and glycerine); and panthenol dissolved in glycerine, flavor oils and mixtures thereof. Mixtures of these solvents can also be used. Exemplary polar solvents may be polyhydric alcohols and water. Examples of solvents may include glycerine, panthenol in glycerine, glycols such as propylene glycol and butylene glycol, polyethylene glycols, water and mixtures thereof. Additional polar solvents for use may be alcohols, glycerine, panthenol, propylene glycol, butylene glycol, hexylene glycol and mixtures thereof.

An emollient may also be added to the cosmetic/dermatological compositions described herein. The emollient component can comprise fats, oils, fatty alcohols, fatty acids and esters which aid application and adhesion, yield gloss and provide occlusive moisturization. Suitable emollients for use may be isostearic acid derivatives, isopropyl palmitate, lanolin oil, diisopropyl dimerate, maleated soybean oil, octyl palmitate, isopropyl isostearate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl linoleate, pentaerythrityl tetrastearate, neopentylglycol dicaprylate/dicaprate, hydrogenated coco-glycerides, isononyl isononanoate, isotridecyl isononanoate, myristyl myristate, triisocetyl citrate, cetyl alcohol, octyl dodecanol, oleyl alcohol, panthenol, lanolin alcohol, linoleic acid, linolenic acid, sucrose esters of fatty acids, octyl hydroxystearate and mixtures thereof. Examples of other suitable emollients can be found in the Cosmetic Bench Reference, pp. 1.19-1.22 (1996), or in the International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., 7.sup.th Edition, 1997) (hereinafter "ICI Handbook"), incorporated herein by reference. Suitable emollients may include polar emollient emulsifiers (such as linear or branched chained polyglycerol esters) and non-polar emollients. The emollient component typically may comprise from about 1% to about 90%, preferably from about 10% to about 80%, more preferably from about 20% to about 70%, and most preferably from about 40% to about 60%, of the cosmetic composition.

By "polar emollient," as used herein, is meant any emollient emulsifier having at least one polar moiety and wherein the solubility (at 30° C.) of the cytoprotective derivative compound in the polar emollient is greater than about 1.5%, preferably greater than about 2%, more preferably greater than about 3%. Suitable polar emollients may include, but are not limited to, polyol ester and polyol ethers such as linear or branched chained polyglycerol esters and polyglycerol ethers. Non-limiting examples of such emollients may include PG3 diisostearate, polyglyceryl-2-sesquiisostearate, polyglyceryl-5-distearate, polyglyceryl-10-distearate, polyglyceryl-10-diisostearate, acetylated monoglycerides, glycerol esters, glycerol tricaprylate/caprate, glyceryl ricinoleate, glyceryl isostearate, glyceryl myristate, glyceryl linoleate, polyalkylene glycols such as PEG 600, monoglycerides, 2-monolaurin, sorbitan esters and mixtures thereof.

By "non-polar emollient," as used herein, means any emollient emulsifier possessing no or minimal permanent electric moments. Suitable non-polar emollients may include, but are not limited to, esters and linear or branched chained hydrocarbons. Non-limiting examples of such emollients may include isononyl isononanoate, isopropyl isostearate, octyl hydroxystearate, diisopropyl dimerate, lanolin oil, octyl palmitate, isopropyl palmitate, paraffins, isoparaffins, acetylated lanolin, sucrose fatty acid esters, isopropyl myristate, isopropyl stearate, mineral oil, silicone oils, dimethicone, allantoin, isohexadecane, isododecane, petrolatum, and mixtures thereof. The solubility of the compound in polar or non-polar emollients may be determined according to methods known in the art.

Suitable oils include esters, triglycerides, hydrocarbons and silicones. These can be a single material or a mixture of one or more materials. They may normally comprise from 0.1% to about 100%, preferably from about 5% to about 90%, and most preferably from about 70% to about 90% of the emollient component.

Oils that act as emollients also impart viscosity, tackiness, and drag properties to cosmetic compositions such as lipstick. Examples of suitable oils may include acrylic triglycerides; caprice triglyceride; isostearyl triglyceride; atopic triglyceride; propylene glycol myristyl acetate; lanolin; lanolin oil; polybutene; isopropyl palmitate; isopropyl myristate; isopropyl isostearate; diethyl sebacate; diisopropyl adipate; tocopheryl acetate; tocopheryl linoleate; hexadecyl stearate; ethyl lactate; cetyl oleate; cetyl ricinoleate; oleyl alcohol; hexadecyl alcohol; octyl hyroxystearate; octyl dodecanol; wheat germ oil; hydrogenated vegetable oils; castor oil; petrolatum; modified lanolins; branched-chain hydrocarbons; alcohols and esters; corn oil; cottonseed oil; olive oil; palm kernel oil; rapeseed oil; safflower oil; jojoba oil; evening primrose oil; avocado oil, mineral oil, shea butter, octylpalmitate, maleated soybean oil, glycerol trioctanoate, diisopropyl dimerate, and volatile and non-volatile silicone oils including phenyl trimethicone.

Suitable oils for use herein may be acetylglycerides, octanoates, and decanoates of alcohols and polyalcohols, such as those of glycol and glycerol, the ricinoleates of alcohols and polyalcohols such as cetyl ricinoleate, PG-3 diisostearate, polyglycerol ethers, polyglyerol esters, caprylic triglycerides, capric triglycerides, isostearic triglyceride, adipic triglyceride, phenyl trimethicone, lanolin oil, polybutene, isopropyl palmitate, isopropyl isostearate, cetyl ricinoleate, octyl dodecanol, oleyl alcohol, hydrogenated vegetable oils, castor oil, modified lanolins, octyl palmitate, lanolin oil, maleated soybean oil, cetyl ricinoleate, glyceryl trioctanoate, diisopropyl dimerate, synthetic lanolin derivatives and branched chain alcohols, sucrose esters of fatty acids, octyl hydroxystearate and mixtures thereof.

Preferably, the oils used may be selected such that the majority (at least about 75%, preferably at least about 80% and most preferably at least about 99%) of the types of oils used have solubility parameters that do not differ by more than from about 1 to about 0.1, preferably from about 0.8 to about 0.1.

A surfactant may also be added to compositions described herein, in order to confer beneficial cosmetic or application properties. Surfactants suitable for use may be those which can form emulsions and/or association structures. Surfactant emulsifier can be from 0% to about 20% of the formulation, preferably from 0% to about 15% and most preferably from about 1% to about 10%. Examples of suitable emulsifiers can be found in U.S. Pat. No. 5,085,856 to Dunphy et al., and U.S. Pat. No. 5,688,831 to El-Nokaly et al. Examples of other suitable emulsifiers can be found in Cosmetic Bench Reference, pp. 1.22, 1.24-1.26 (1996), all of which are incorporated herein by reference.

Examples of surface active agents which may be used in the compositions described herein include sodium alkyl sulfates, e.g., sodium lauryl sulfate and sodium myristyl sulfate, sodium N-acyl sarcosinates, e.g., sodium N-lauroyl sarcosinate and sodium N-myristoyl sarcosinate, sodium dodecylbenzenesulfonate, sodium hydrogenated coconut fatty acid monoglyceride sulfate, sodium lauryl sulfoacetate and N-acyl glutamates, e.g., N-palmitoyl glutamate, N-methylacyltaurin sodium salt, N-methylacylalanine sodium salt, sodium alpha-olefin sulfonate and sodium dioctylsulfosuccinate; N-alkylaminoglycerols, e.g., N-lauryl-diamino-ethylglycerol and N-myristyldiaminoethylglycerol, N-alkyl-N-carboxymethylammonium betaine and sodium 2-alkyl-1-hydroxyethylimidazoline betaine; polyoxyethylenealkyl ether, polyoxyethylenealkylaryl ether, polyoxyethylenelanolin alcohol, polyoxyethyleneglyceryl monoaliphatic acid ester, polyoxyethylenesorbitol aliphatic acid ester, polyoxyethylene aliphatic acid ester, higher aliphatic acid glycerol ester, sorbitan aliphatic acid ester, Pluronic type surface active agent, and polyoxyethylenesorbitan aliphatic acid esters such as polyoxyethylenesorbitan monooleate and polyoxyethylenesorbitan monolaurate. Emulsifier-type surfactants known to those of skill in the art can be used in the compositions described herein.

Also useful herein may be surfactants that form association structures, preferably lamellar or hexagonal liquid crystals, at ambient temperature when mixed with a polar solvent. In preparing a sample combination of surfactant and polar solvent to demonstrate the ability to form association structures, the surfactant needs to be sufficiently soluble in the polar solvent such that an association structure can form at ambient temperature. One of ordinary skill in the art is capable of determining compatible interactions.

Any surfactant which forms association structures at ambient temperature and is suitable for use in cosmetics may be suitable for use herein. Surfactants suitable for use in cosmetics present no or minimal dermatological or toxicological problems. Anionic surfactants, nonionic surfactants, cationic surfactants, amphoteric surfactants and mixtures thereof may be suitable for use. Preferably anionic surfactants, nonionic surfactants, cationic surfactants, amphoteric surfactants and mixtures thereof having a Krafft point at or below about ambient temperature are used. More preferably, nonionic surfactants, cationic surfactants, amphoteric surfactants and mixtures thereof having a Krafft point at or below about ambient temperature are used.

The surfactants can be used at levels from about 4% to about 97%, preferably from about 5% to about 95%, more preferably from about 20% to about 90% and most preferably from about 30% to about 70% of the association structure.

The cosmetic compositions described herein may contain one or more materials, herein singly or collectively referred to as a "solidifying agent", that are effective to solidify the particular liquid base materials to be used in a cosmetic composition. (As used herein, the term "solidify" refers to the physical and/or chemical alteration of the liquid base material so as to form a solid or semi-solid at ambient conditions, i.e., to form a final composition that has a stable physical structure and can be deposited on the skin under normal use conditions.) As is appreciated by those skilled in the art, the selection of the particular solidifying agent for use in the cosmetic compositions will depend upon the particular type of composition desired, i.e., gel or wax-based, the desired rheology, the liquid base material used and the other materials to be used in the composition. The solidifying agent can be preferably present at a concentration of from about 0.1% to about 90%, more preferably from about 1% to about 50%, even more preferably from about 5% to about 40%, most preferably from about 3% to about 20%.

The wax cosmetic stick variations provided herein preferably may contain from about 5% to about 50% (by weight) of a waxy solidifying agent. By the term "waxy solidifying agent," as used herein, is meant a solidifying material having wax-like characteristics. Such waxy materials may also serve as emollients. Among the waxy materials useful herein are the high melting point waxes, i.e., having a melting point of from about 65° C. to about 125° C., such as beeswax, spermaceti, carnauba, bayberry, candelilla, montan, ozokerite, ceresin, paraffin, synthetic waxes such as Fisher-Tropsch waxes, microcrystalline wax, and mixtures thereof. Ceresin, ozokerite, white beeswax, synthetic waxes, and mixtures thereof, are among those useful herein; additional useful waxes are disclosed in U.S. Pat. No. 4,049,792, Elsnau, issued Sep. 20, 1977, herein incorporated by reference in its entirety. Low melting waxes, having a melting point of from about 37° C. to about 75° C., may be preferred for use in the wax stick variations described herein. Wax stick variations, which contain volatile silicone oils as a liquid base material, preferably contain from about 10% to about 35%, more preferably from about 10% to about 20% (by weight), of a low-melting wax. Such materials include fatty acids, fatty alcohols, fatty acid esters and fatty acid amides, having fatty chains of from about 8 to about 30 carbon atoms, and mixtures thereof. Wax-like materials include cetyl alcohol, palmitic acid, stearyl alcohol, behenamide, sucrose esters of tallow fatty acids, mono and di-fatty acid esters of polyethylene glycol, and mixtures thereof. Stearyl alcohol, cetyl alcohol, and mixtures thereof, are mostly used. Additional fatty acids, fatty alcohols, and other wax-like materials are also well known in the art.

In addition, these compositions may include other medicinal agents, therapeutic agents, carriers, adjuvants, and the like. Some particular additional agents may include sunscreens; retinoids; antioxidants; hydroxyacids; fatty acids, acceptable non-toxic metal salts of naturally occurring amino acids or of hydroxyalkyl acids; botanical extracts, salicylic acid, benzoyl peroxide, antibiotics, antiandrogens, anti-inflammatory agents, antioxidants, ascorbic acid, vitamins B, tocopherols or tocotrienols, corticosteroids, moisteners, surfactants, keratolytic agents, complexing agents, colorants, fragrances, and mixtures thereof.

Measurement of Skin Pigmentation and Coloration

Measurements of skin pigmentation and coloration can be quantitated using a chromameter, colorimeter, or skin reflectance instrument (see, for example, Clarys et al., Skin Res. Technol. 6(4):230-238 (2000)). Chromameters are commercially available from vendors such as Konica Minolta (CR-400 or CR-410 Chroma Meter) or Gigahertz-Optik (HCT-99D color meter). Baseline readings prior to treatment are taken, and readings during treatment can be taken, at one or more wavelengths. Skin coloration can be measured and compared to assess treatment. Measurements can be taken at various points, such as an area affected by discoloration and a surrounding unaffected area.

Synthetic Methods

The resorcinol compounds described herein can be synthesized by an appropriate combination of generally well-known synthetic methods. Techniques useful in synthesizing the compounds herein are both readily apparent and accessible to those of skill in the relevant art in light of the teachings described herein. The discussion below is offered to illustrate certain of the diverse methods available for use in assembling the compounds herein. However, the discussion is not intended to limit the scope of reactions or reaction sequences that are useful in preparing the compounds herein.

The resorcinol compounds described herein may be synthesized according to Scheme 1. Reactant $C(O)R^2$ indicates a reactant having a carbonyl group; that is, the $C=O$ group is a part of $R^2$, and not an additional moiety appended to $R^2$. Appropriate protecting groups (PG in the scheme below), such as alkyl groups, may be used to protect certain functional groups from reaction conditions, and such protecting groups are removed under standard conditions when appropriate.

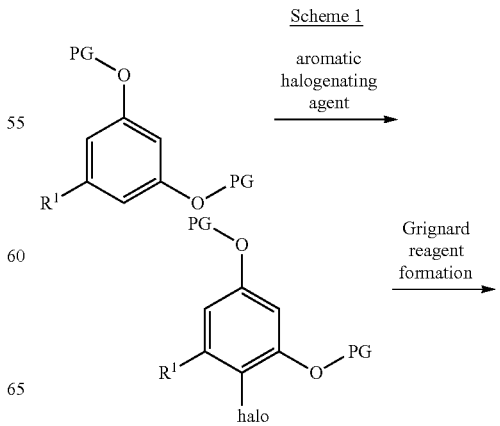

Scheme 1

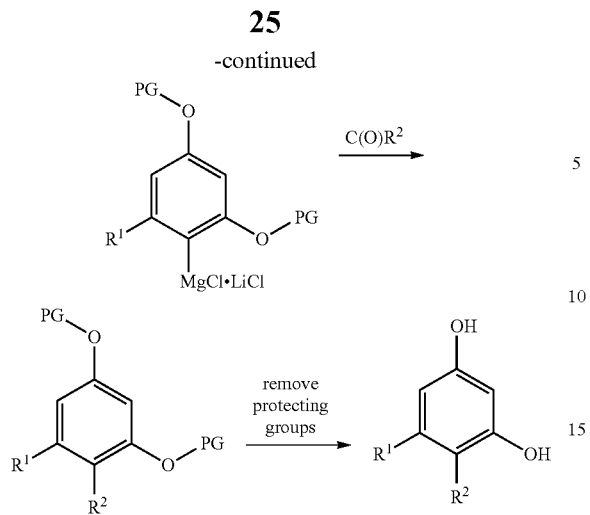

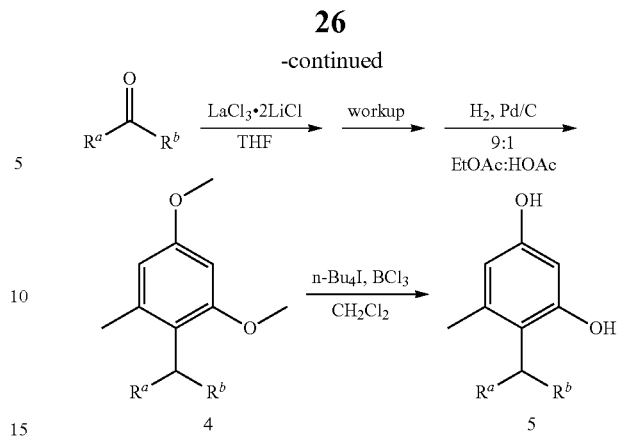

Scheme 2 shows an exemplary synthesis of a 5-methyl resorcinol compound described herein according to Scheme 1. $R^a$ and $R^b$ are each hydrogen or substituted or unsubstituted alkyl, wherein the substituted or unsubstituted alkyl groups may be the same or different, or $R^a$ and $R^b$, together with the carbon to which they are attached, form a substituted or unsubstituted cycloalkyl. Compound 1 (commercially available from Sigma-Aldrich, St. Louis, Mo.) is brominated, for example with N-bromosuccinimide, to afford compound 2, which is reacted with magnesium to form Grignard reagent 3. Compound 3 is reacted with an alkyl ketone in the presence of lanthanum salts, followed by reduction by hydrogen over Pd/C to form compound 4. The alkoxy groups are then converted to hydroxy groups to afford resorcinol compound 5.

Scheme 3 shows an exemplary synthesis of a 5-fluoro resorcinol compound described herein according to Scheme 1. $R^c$ and $R^d$ are each hydrogen or substituted or unsubstituted alkyl, wherein the substituted or unsubstituted alkyl groups may be the same or different, or $R^c$ and $R^d$, together with the carbon to which they are attached, form a substituted or unsubstituted cycloalkyl. Compound 6 (commercially available from Sigma-Aldrich, St. Louis, Mo.) is brominated to afford compound 7, which is reacted with magnesium to form Grignard reagent 8. Compound 8 is reacted with an alkyl ketone in the presence of lanthanum salts to form compound 9, followed by reduction by hydrogen over Pd/C to form compound 10. The alkoxy groups are then converted to hydroxy groups to afford resorcinol compound 11. Similar methods can be used to synthesize other 4-halo resorcinols.

Scheme 2

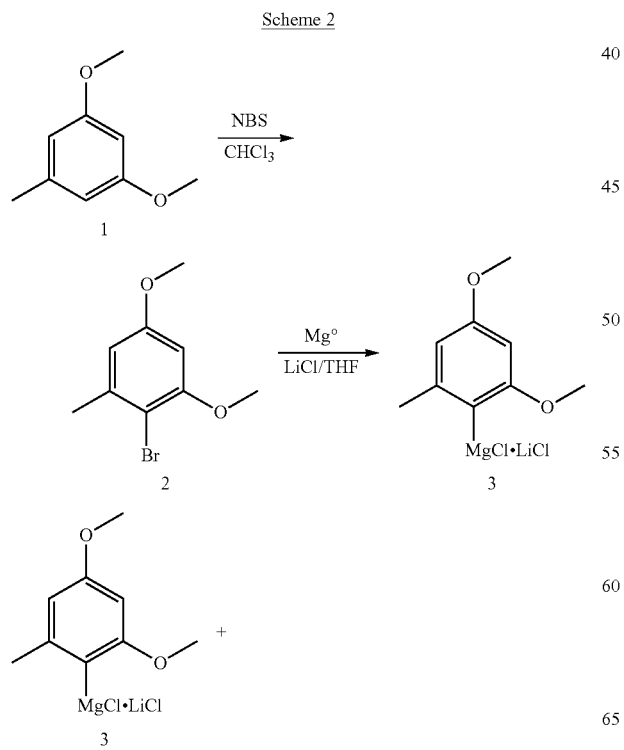

Scheme 3

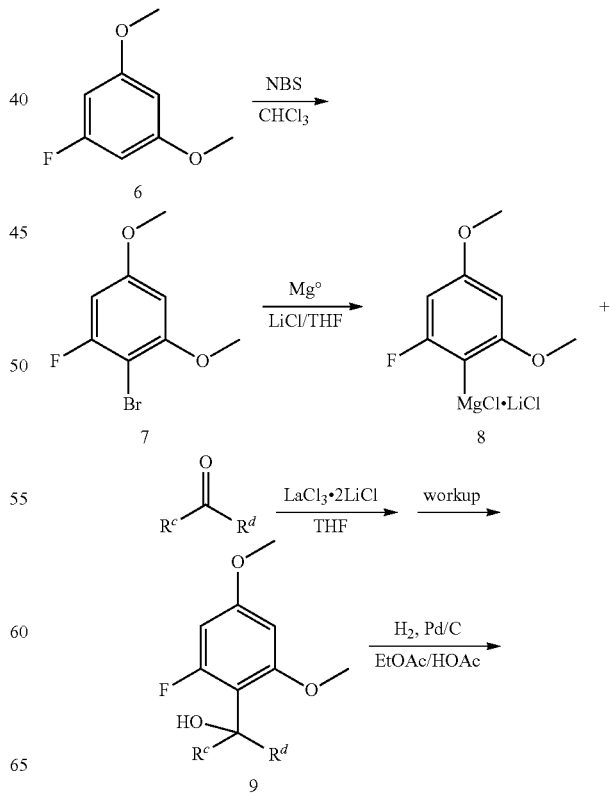

27
-continued

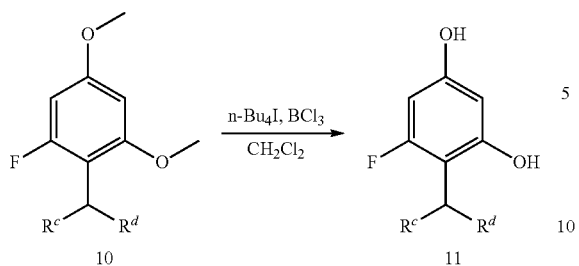

28
-continued

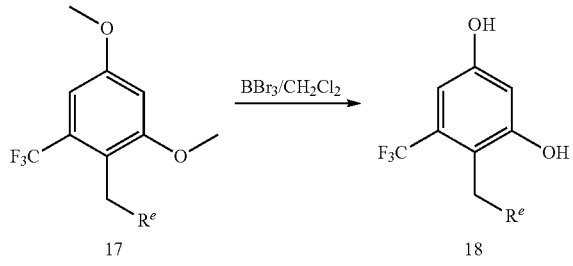

Scheme 4 shows an exemplary synthesis of a 4-alkyl-5-trifluoromethyl resorcinol compound described herein according to Scheme 1. $R^e$ is substituted or unsubstituted alkyl. Bromide compound 12 is converted to the corresponding iodide 13, which is reacted with an acyl chloride to form ketone 14. Compound 14 is reacted with difluoro-fluorosulfonyl-acetic acid methyl ester (15) to form compound 16, followed by reduction by zinc in the presence of acid (or other suitable reducing agent) to form compound 17. The alkoxy groups are then converted to hydroxy groups to afford resorcinol compound 18. Similar methods can be used to synthesize other 4-alkyl-5-trifluoromethyl resorcinols.

Scheme 5 shows an exemplary synthesis of a 4-cycloalkyl-5-trifluoromethyl resorcinol compound described herein according to Scheme 1. A represents a substituted or unsubstituted cycloalkenyl ring, and B represents the corresponding substituted or unsubstituted cycloalkyl ring. Bromide compound 19 is converted to the corresponding iodide 20. Compound 20 is reacted with difluoro-fluorosulfonyl-acetic acid methyl ester to form compound 21, followed by bromination with NBS to form compound 22. Cycloalkenyl A is installed using an appropriate dioxaborolane to form compound 23, which is reduced in the presence of Pd/C (or other suitable reducing agent) to form compound 24. The alkoxy groups are then converted to hydroxy groups to afford resorcinol compound 25. Similar methods can be used to synthesize other 4-cycloalkyl-5-trifluoromethyl resorcinols.

Scheme 4

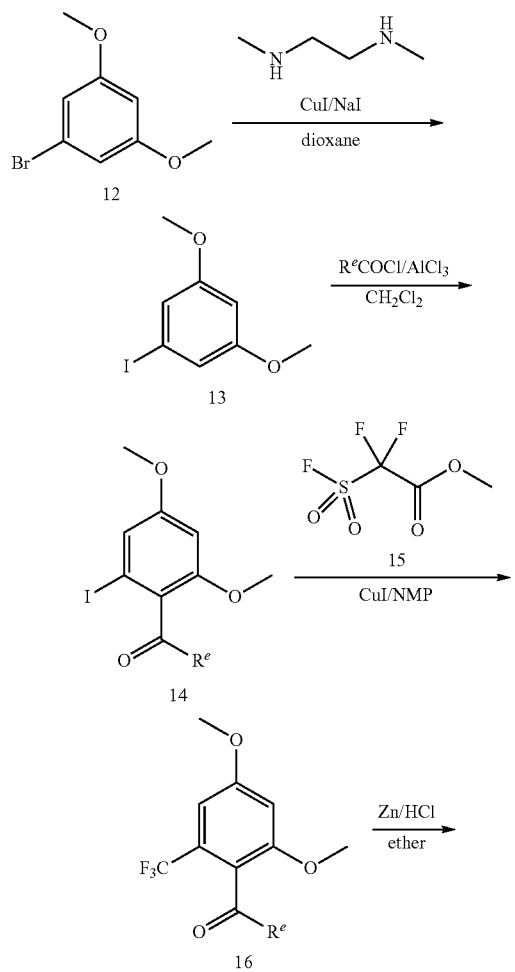

Scheme 5

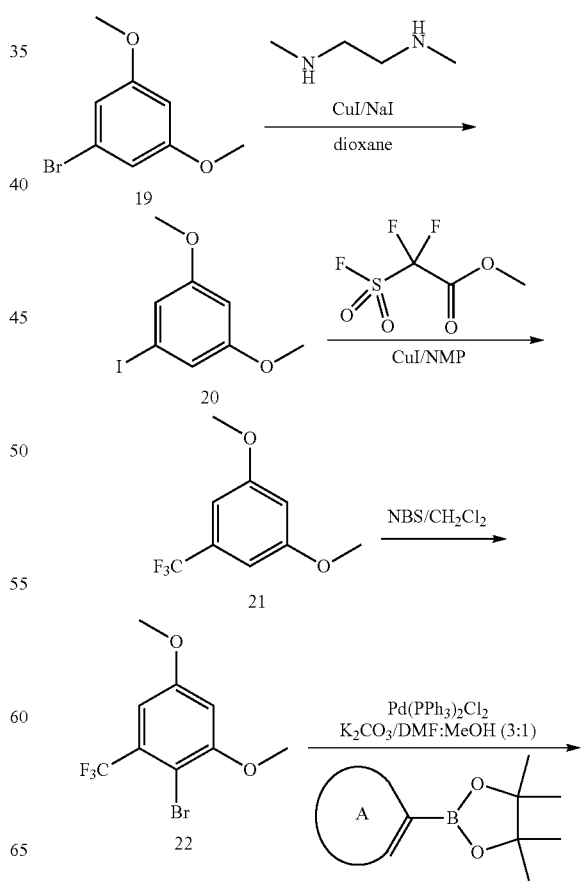

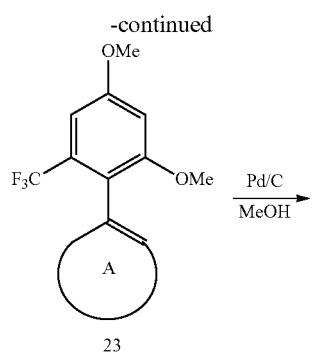

23

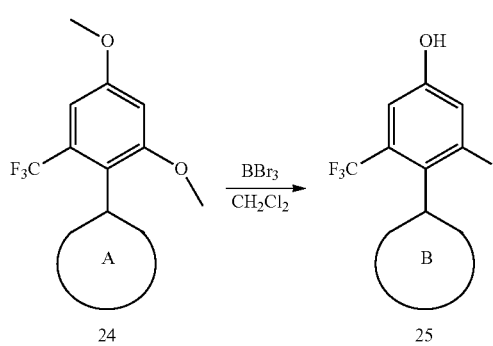

24 → 25

EXAMPLES

Example 1

4-cyclohexyl-5-methylbenzene-1,3-diol (4,5CHMR)

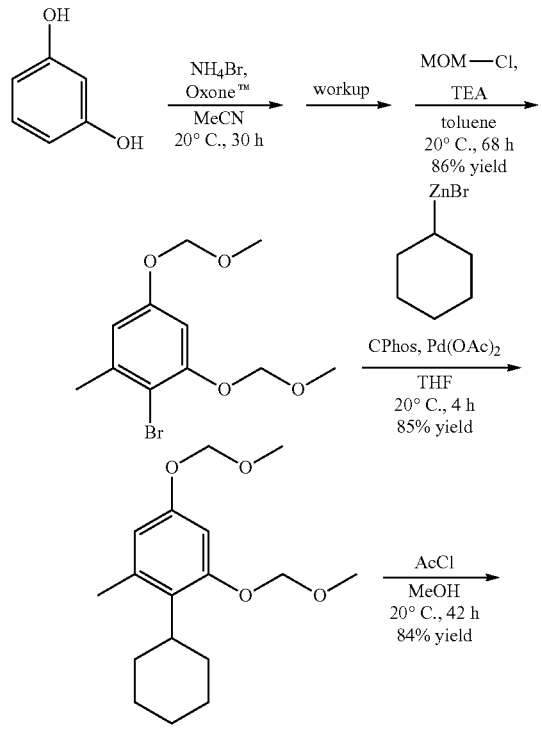

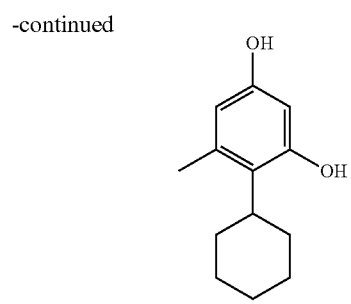

4-bromo-1,5-bis(methoxymethoxy)-3-methylbenzene.

26.10 g of orcinol and 19.10 g of ammonium bromide were weighed into a 2000 mL 3-neck round bottom flask fitted with a stir bar, thermometer, and nitrogen bubbler. A nitrogen atmosphere was established and maintained. 1000 mL of acetonitrile was added, and the mixture was stirred rapidly to suspend the solids. The suspension was cooled to 10° in an ice bath and 67.88 g of Oxone™ (OXONE is a registered trademark of DuPont for a monopersulfate oxidizing compound) was added in one portion. The ice bath was removed, and the mixture was stirred at 20° for 30 h. The solids were removed by filtration. The solvent was removed from the filtrate to obtain a dark orange solid. The solid was partitioned between 200 mL of 1.0 M hydrochloric acid and 400 mL tert-butyl methyl ether. The phases were separated, and the aqueous phase was extracted with 200 mL tert-butyl methyl ether. The combined organic phases were washed with 5×200 mL of 1.0 M pH 5.5 phosphate buffer and 200 mL of brine. 1.0 g of activated carbon was added to the solution, and the solution was dried over sodium sulfate. The solution was filtered through a 10 cm diameter Buchner funnel containing a 2-layer filter pad of 5 cm silica gel on top of 2 cm of Celite™ (CELITE is a registered trademark of Imerys Minerals California, Inc. for a diatomaceous earth-containing filter aid). The filter pad was washed with 2×300 mL of tert-butyl methyl ether. The solvent was removed from the filtrate to obtain 38.78 g of a brown-orange solid. The solid was recrystallized from 1,2-dichloroethane and dried under vacuum to obtain 35.30 g of a 7:88:4 mixture of unbrominated:monobrominated:dibrominated orcinols as brown crystals. 32.95 g of the crystals were dissolved in 100 mL of anhydrous ethyl acetate, and the solution was added dropwise to a solution of chloromethyl methyl ether prepared as described below.

A three-necked 1000-mL flask was fitted with a magnetic stir bar, thermometer, addition funnel, efficient reflux condenser with nitrogen inlet, and gas outlet bubbler quenched into 1.0 M aqueous sodium hydroxide. A nitrogen atmosphere was established and maintained. The flask was charged with 46.65 g of dimethoxymethane and 180 mL of anhydrous toluene. 16 mg of zinc bromide was added. 47.2 g of acetyl chloride was added dropwise over 10 minutes. The addition funnel was rinsed with 20 mL of toluene directly into the reaction mixture. The reaction mixture was stirred at 20° for 4.5 h. The resulting solution of chloromethyl methyl ether was cooled with an ice bath, and 100 mL of N,N-diisopropylethylamine was added dropwise over 20 min. The solution of 32.95 g of brominated orcinols in 100 mL ethyl acetate prepared above was added dropwise at a rate to maintain the reaction temperature below 10°. A white precipitate formed during the addition. The ice bath was removed, and the mixture was stirred at 20° for 68 h. The reaction was quenched with 100 mL of saturated aqueous ammonium chloride. 50 mL of water was added to bring all the salts into solution. The biphasic mixture was stirred vigorously for 3 h to ensure all residual chloromethyl methyl ether was decomposed. The phases were separated, and the aqueous phase was extracted with 250 mL of ethyl acetate. The combined organic phases were washed with 2×200 mL of 1.0 M aqueous citric acid, 3×200 mL of 1.0 M aqueous sodium hydroxide, and 250 mL of brine. The solution was dried over sodium sulfate and the solvent was removed to obtain 47.87 g of a red liquid. 45.34 g of the crude was purified by vacuum distillation to obtain 35.91 g [86% yield calculated from orcinol] of the title compound as a pale yellow liquid, Bp 92-94°/0.046 Torr. $^1$H-NMR (400 MHz, CDCl$_3$) δ 6.69 (d, J=2.7 Hz), 6.64 (d, J=2.7 Hz), 5.20 (s, 2H), 5.11 (s, 2H), 3.50 (s, 3H), 3.45 (s, 3H), 2.37 (s, 3H).

4-cyclohexyl-1,5-bis(methoxymethoxy)-3-methylbenzene. 1.12 g of 2-dicyclohexylphosphino-2',6'-bis(N,N-dimethylamino)biphenyl, 0.28 g of palladium(II) acetate, and 18.50 g of 4-bromo-1,5-bis(methoxymethoxy)-3-methylbenzene (1) were weighed into a 1000 mL oven dried 3-neck round bottom flask fitted with a stir bar, thermometer, addition funnel, and nitrogen bubbler. A nitrogen atmosphere was established and maintained. 200 mL of anhydrous THF was added, and the mixture was stirred to obtain a clear ruby solution. The solution was cooled with an ice bath, 150 mL of a 0.5 M solution of cyclohexylzinc bromide in THF was added over 60 min, keeping the reaction temperature below 5° C. The cooling bath was removed when the addition was complete, and the mixture was stirred at ambient temperature for 4 h. The solution was cooled in an ice bath and quenched with 350 mL of saturated aqueous ammonium chloride. The phases were separated, and the aqueous phase was extracted with 350 mL of cyclopentyl methyl ether. The combined organic phases were filtered through Celite™ to remove fine particulates. The filtrate was washed with 2×300 mL of 1.0 M citric acid, 300 mL of saturated aqueous sodium bicarbonate, and 300 mL of brine, and dried over sodium sulfate and removed the solvent to obtain a dark red liquid. The liquid was diluted with 100 mL of heptane and filtered through a 5 cm thick×9.5 cm diameter silica gel pad. The product was washed through with 1000 mL of 25% EtOAc/heptane. The solvent was removed from the filtrate. The amber liquid was purified by vacuum distillation to obtain 15.83 g [85% yield] of the title compound as a clear colorless oil, Bp 114-116° C./0.056 Torr. $^1$H-NMR (400 MHz, CDCl$_3$) δ 6.63 (d, J=2.5 Hz), 6.49 (d, J=2.5 Hz), 5.13 (s, 2H), 5.10 (s, 2H), 3.47 (s, 3H), 3.45 (s, 3H), 2.77 (br s, 1H), 2.29 (s, 3H), 2.10-1.95 (m, 2H), 1.83-1.75 (m, 2H), 1.73-1.66 (m, 1H), 1.59-1.52 (m, 2H), 1.37-1.18 (m, 3H).

4-cyclohexyl-5-methylbenzene-1,3-diol (4,5CHMR). 15.78 g of 4-cyclohexyl-1,5-bis(methoxymethoxy)-3-methylbenzene (2) was weighed into an oven dried 1000 mL flask fitted with a stir bar, septum and nitrogen bubbler. A nitrogen atmosphere was established and maintained. Added 400 mL of anhydrous methanol. Cooled the solution below 5° C. Added 7.7 mL of acetyl chloride over 30 min, keeping the reaction temperature below 5° C. Removed the cooling bath when the addition was complete and stirred at 20° C. for 42 h. Removed the volatiles on a rotary evaporator to obtain a yellow resin. Dissolved the resin in 75 mL MTBE and diluted with 75 mL heptane. Removed baseline impurities by passing the solution through 220 g of silica gel, washing the product through with 800 mL of 50% MTBE/heptane. Removed the solvent on a rotary evaporator to obtain a pale yellow solid. The solid was recrystallized twice from 50 mL of 1,2-dichloroethane. Dried under vacuum at 85°/0.05 Torr to obtain 9.33 g [84% yield] of the title compound as fine white needles. 300 mg of this material was purified by sublimation at 130°/0.03 Torr to obtain an analytical standard. $^1$H-NMR (400 MHz, DMSO-d$_6$) δ 8.74 (overlapping singlets, 2H), 6.07 (d, J=2.5 Hz), 5.98 (d, J=2.4 Hz), 2.64 (br s, 1H), 2.17-1.98 (methyl singlet at 2.12 overlaps multiplet, 5H), 1.77-1.68 (m, 2H), 1.68-1.60 (m, 1H), 1.46-1.34 (m, 2H), 1.34-1.10 (m, 3H).

Example 2

4-cyclohexyl-5-fluorobenzene-1,3-diol (4,5CHFR)

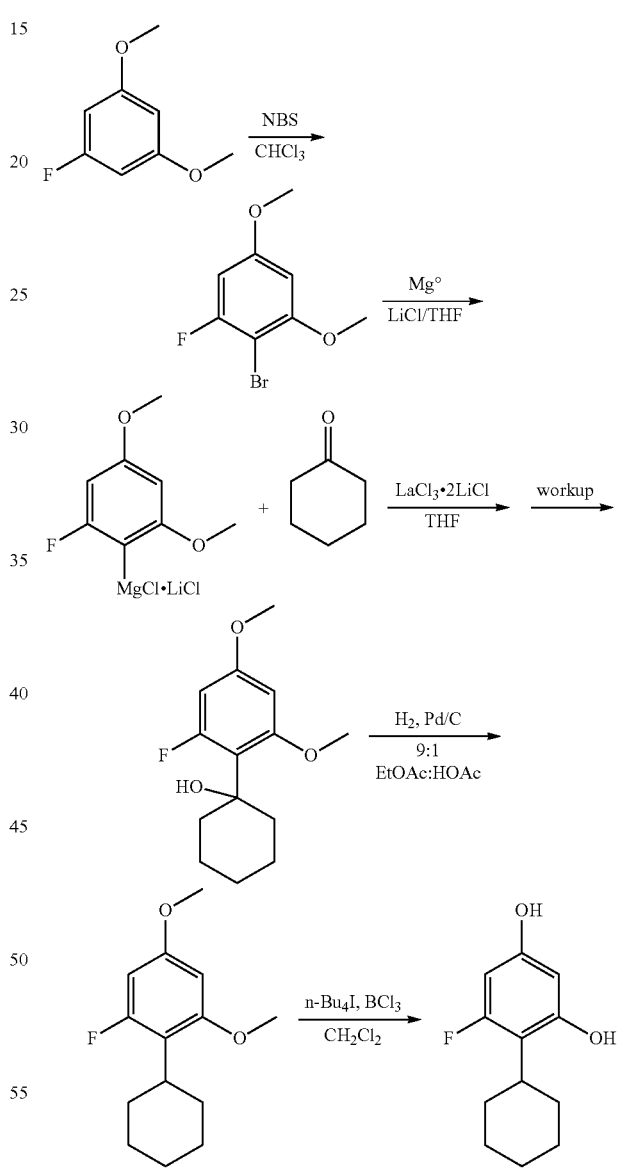

2-bromo-1-fluoro-3,5-dimethoxybenzene. 28.22 g of 3,5-dimethoxy-5-fluorobenzene was weighed into a 1,000 mL round bottom flask fitted with a stir bar, reflux condenser, nitrogen inlet, and cap. A nitrogen atmosphere was established and maintained throughout the reaction. 200 mL of anhydrous CCl$_4$ was added, followed by 32.61 g of N-bromosuccinimide (NBS). The remaining NBS powder residue was washed into the flask with 100 mL of CCl$_4$. The reaction mixture was stirred at reflux under N, for 4 h, during which time the suspended yellow solids changed color to white. At completion, the precipitated succinimide solids were filtered off and washed thoroughly with 200 mL heptane. The CCl$_4$ was removed from the filtrate by rotary evaporation at 50° C. More succinimide precipitated from the heptane solution and was removed by filtration while the solution was still warm. The remaining heptane was removed in vacuo to obtain a clear, amber oil (40.67 g), which solidified on standing. Purification of the crude material was accomplished by distillation. The condenser was kept at 50° C. to prevent the product from solidifying before reaching the collection flask. After a small impurity fraction was collected at 78° C./8 torr, the product distilled at 123-125° C./8 torr. The clear pale yellow liquid solidified to an off-white solid on standing (37.88 g, 89%).

1-(2-fluoro-4,6-dimethoxyphenyl)cyclohexanol. 19.52 g of 2-bromo-1-fluoro-3,5-dimethoxybenzene was weighed into an oven-dried 500 mL round bottom flask fitted with a stir bar, septum, thermometer, and nitrogen inlet. A nitrogen atmosphere was established and maintained. To the solution was slowly added 200 mL of a 0.5 M solution of lithium chloride in anhydrous THF. The clear pale yellow solution was placed in a water ice/acetone bath and the reaction temperature was maintained between −15° C. and −10° C. To the reaction mixture was added 45 mL of a 2.0 M (iodometric titration) solution of isopropyl magnesium chloride in diethyl ether, dropwise over 20 min using a syringe pump. The reaction was stirred between −20° C. and −15° C. for 60 min. The solution rapidly became colorless at the start of addition, then slowly became a clear yellow color. LC-MS analysis of an aliquot quenched in 5% H$_2$O/MeOH at 60 min indicated the reaction was 50% complete. At this point, 5 mL of a 2.0 M solution of isopropylmagnesium chloride in Et$_2$O was added via syringe. LC-MS analysis of an aliquot quenched in 5% H$_2$O/MeOH 60 min after the addition indicated the reaction was 80% complete. After waiting another 30 min, the clear yellow solution was transferred into the next reaction via cannula.

7.48 g of cyclohexanone was weighed into an oven-dried 1,000 mL 3-neck round bottom flask fitted with a stir bar, septum, thermometer, and nitrogen inlet. A nitrogen atmosphere was established and maintained. To the solids was added 125 mL of a 0.6 M solution of lanthanum trichloride complex with 2 equivalents of lithium chloride in anhydrous THF. The solution was stirred at room temperature for 2.5 h. Following this period, the clear amber solution was cooled in a water ice/acetone bath and the solution temperature was maintained between −5° C. and 0° C. during addition. The above-described solution of 2,4-dimethoxy-6-methylphenyl magnesium chloride complex with lithium chloride was transferred into the reaction mixture by cannula. The amber reaction mixture was stirred between 0° C. and 5° C. for 2 h. The reaction mixture was cooled to −10° and quenched by adding a mixture of 100 g of ice in 100 mL of saturated aqueous NH$_4$Cl. A moderate exotherm raised the temperature to 5° C. before cooling down again. A white emulsion formed in the aqueous layer. To the mixture was added 20 mL of concentrated hydrochloric acid. The emulsion did not dissolve. The phases were separated, and the aqueous phase was back-extracted with 2×200 mL of MTBE. The combined organics were washed with 1×200 mL of a mixture of 1:1 brine and 1 M aqueous NaOH. A small amount of gummy orange material separated at the solvent interface and was discarded. The remaining organic phase was washed with 200 mL brine and dried over Na$_2$SO$_4$. Excess solvent was removed in vacuo to obtain 21.96 g of a dark amber liquid. The liquid was diluted with 25 mL heptane and purified by chromatography on a 450 g Supelco VersaPak™ silica gel column (gradient elution from 0 to 33% ethyl acetate/heptane over 15 column volumes). Isolated 13.14 g, pale yellow liquid (68% yield).

2-cyclohexyl-1-fluoro-3,5-dimethoxybenzene. 13.04 g of 1-(2-fluoro-4,6-dimethoxyphenyl)cyclohexanol was weighed into a 500 mL round bottom flask fitted with a stir bar and septum cap. To the solids was added 250 mL of 9:1 EtOAc:HOAc. The solution was sparged with nitrogen for 5 min and charged with 2.58 g of 10 wt % palladium on carbon. A hydrogen atmosphere over the reaction mixture was established and maintained with a balloon. The reaction was stirred at 70° C. for 20 h, after which LC-MS analysis indicated the reduction was complete. The catalyst was removed by filtration through a Whatman GF/B glass fiber filter and the solids washed thoroughly with 200 mL EtOAc. The filtrate was poured into a separatory funnel and washed with 200 mL of 2.5 M aqueous sodium hydroxide, 200 mL of water, and 200 mL of brine, dried over Na$_2$SO$_4$, and concentrated by rotary evaporation to obtain a clear, colorless liquid (11.67 g). The liquid was diluted with heptane and purified by chromatography to obtain 8.67 g of a clear colorless oil (71%).

4-cyclohexyl-5-fluorobenzene-1,3-diol (4,5CHFR). 8.51 g of 4-cyclohexyl-1,3-dimethoxy-5-fluorobenzene and 32.93 g of tetrabutylammonium iodide were weighed into an oven dried 500 mL 2-neck round bottom flask fitted with a stir bar, thermometer, nitrogen inlet, and septum. A nitrogen atmosphere was established and maintained throughout the reaction. To the flask was added 200 mL of anhydrous CH$_2$Cl$_2$. The mixture was cooled to −78° C. in a dry ice/acetone bath. To the rapidly stirred mixture was added 90 mL of a 1.0 M solution of boron trichloride in CH$_2$Cl$_2$ over 30 min using a syringe pump. The mixture was stirred at −78° C. for 15 min, then stirred at −2° C. for 3 h. LC-MS analysis at 2.5 h showed all the starting material had converted to product. The reaction was quenched by slow addition of 100 mL water and the mixture was stirred at room temperature 15 min. At this point, 50 mL of methanol was added to dissolve the solids, and the mixture was stirred at room temperature for 30 min. Organic solvents were removed by rotary evaporation at 50° C. The remaining aqueous mixture was diluted with 400 mL water and extracted with MTBE (3×150 mL). The combined organic layers were extracted with 3×150 mL of 1.0 M aqueous NaOH. The combined aqueous extracts were made acidic by adding 40 mL concentrated hydrochloric acid. The acidic solution was extracted with 3 portions of 150 mL of MTBE. The combined extracts were washed with brine and dried over Na$_2$SO$_4$. Excess solvent was removed on a rotary evaporator. The residue was dissolved in 10% ethyl acetate/ heptane and purified by chromatography on a 330 g Isco RediSep™ silica gel column (gradient elution from 10 to 50% ethyl acetate/heptane). The collected fractions were concentrated and the resulting solids recrystallized from 30 mL of hot 1:1 1,2-dichloroethane:heptane to obtain 3.31 g of colorless orthorhombic crystals. After removal of the solvent from the filtrate, the residue was recrystallized from 12 mL of hot 1:1 1,2-dichloroethane:heptane to obtain a second crop of 2.76 g of small white crystals. A third crop of 472 mg of small pink crystals (the mother liquor is red) was obtained in a similar fashion. The first and second crops were identical by $^1$H-NMR, LC-MS, and TLC and were combined to give the product. White crystalline solid, 6.07 g. 81% yield. $^1$H NMR (DMSO-d$_6$, 400 MHz) δ: 9.43 (d, J=1.4 Hz, 1H), 9.32 (d, J=0.5 Hz, 1H), 6.99 (dd, J=2.3, 1.2 Hz, 1H), 5.91 (dd, J=13, 2.3 Hz, 1H), 2.85 (tt, J=12, 3.3 Hz, 1H), 1.62-1.83 (m, 5H), 1.47-1.57 (m, 2H), 1.10-1.33 (m, 3H).

Example 3

2-Ethyl-1,5-dihydroxy-3-trifluoromethyl-benzene (4,5 ETFMR)

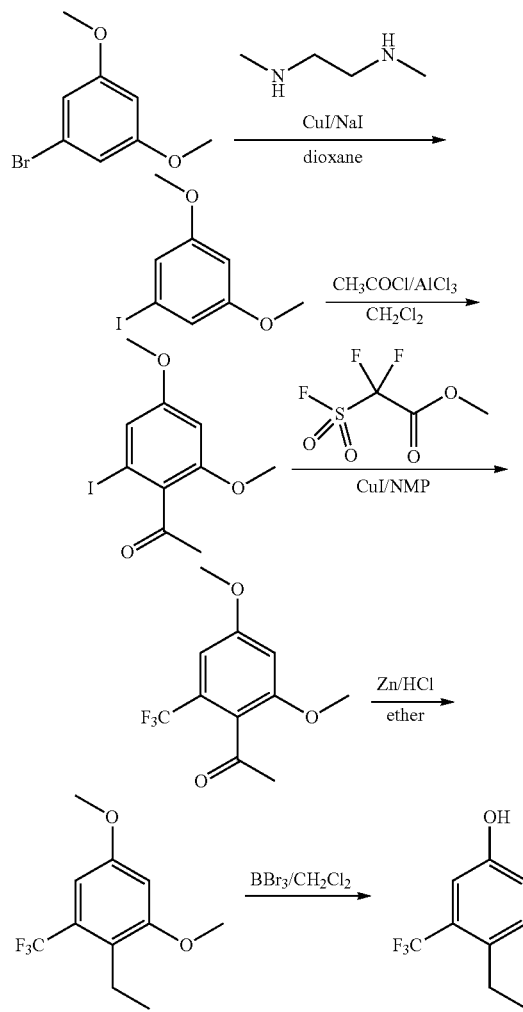

1-(2-Iodo-4,6-dimethoxy-phenyl)-ethanone. To a solution of acetyl chloride (3.12 g, 39 mmol) in dichloromethane (100 mL) was added AlCl$_3$ (6.34 g, 47 mmol) at 0° C. over 30 min. 1-Iodo-3,5-dimethoxy-benzene (10.5 g, 39 mmol) was added to the mixture. The reaction mixture was stirred at room temperature for 1 h. Then ice water (60 mL) was added. The aqueous layer was extracted with dichloromethane (2×30 mL), dried over sodium sulfate and concentrated, and purified by column chromatography (eluted with petroleum ether/ethyl acetate=20:1~1:1), to give the title compound (6 g, 50%).

1-(2,4-Dimethoxy-6-trifluoromethyl-phenyl)-ethanone. A mixture of 1-(2-iodo-4,6-dimethoxy-phenyl)-ethanone (3.17 g, 10.1 mmol), difluoro-fluorosulfonyl-acetic acid methyl ester (7.9 g, 41.1 mmol) and CuI (3.8 g, 20 mmol) in NMP (50 mL) was heated at 120° C. under nitrogen overnight. The mixture was filtered and diluted with water (200 mL), and extracted with ethyl acetate (3×50 mL). The organic layers were washed with brine (50 mL), dried over sodium sulfate and concentrated and purified with column chromatography (eluted with petroleum ether:ethyl acetate=20:1~10:1) to give the title compound (1.6 g, 64%).

2-Ethyl-1,5-dimethoxy-3-trifluoromethyl-benzene. Zinc (8.4 g, 0.13 mol) was added over 10 min to a solution of 1-(2,4-Dimethoxy-6-trifluoromethyl-phenyl)-ethanone (1.6 g, 6.4 mmol) in ethyl ether (20 mL) and concentrated hydrogen chloride (20 mL) at 0° C. The mixture was stirred at room temperature for 2 h. The mixture was filtered off, extracted with ethyl ether (3×50 mL), washed with brine (30 mL), dried over sodium sulfate and concentrated, and purified by column chromatography (eluted with petroleum ether) to give the title compound (0.4 g, 27%).

2-Ethyl-1,5-dihydroxy-3-trifluoromethyl-benzene (4,5 ETFMR). BBr$_3$ (12 mL, 0.67 mol/L) was added to a mixture of 2-ethyl-1,5-dimethoxy-3-trifluoromethyl-benzene (0.4 g, 1.9 mmol) in dichloromethane (10 mL), and the mixture was stirred at room temperature for 4 h. Methanol (5 mL) was added slowly to the mixture at 0° C., and the mixture was concentrated to give an oil residue, which was diluted with water (20 mL), extracted with dichloromethane (4×10 mL), washed with brine (10 mL), concentrated, and purified by pre-HPLC to give the title compound (140 mg, 40%). LC-MS 205 (M−1). $^1$H NMR (400 MHz, CDCl$_3$) δ6.69 (d, J=2.0 Hz, 1H), 6.48 (d, J=2.0 Hz, 1H), 5.06 (s, 1H), 4.99 (s, 1H), 2.70 (q, J=7.6 Hz, 2H), 1.16 (t, J=7.6 Hz, 3H). $^{19}$F NMR (400 MHz, CDCl$_3$) δ−60.2 (s).

Example 4

4-cyclohexyl-3-trifluoromethyl benzene-1,3-diol (4,5CHTFMR)

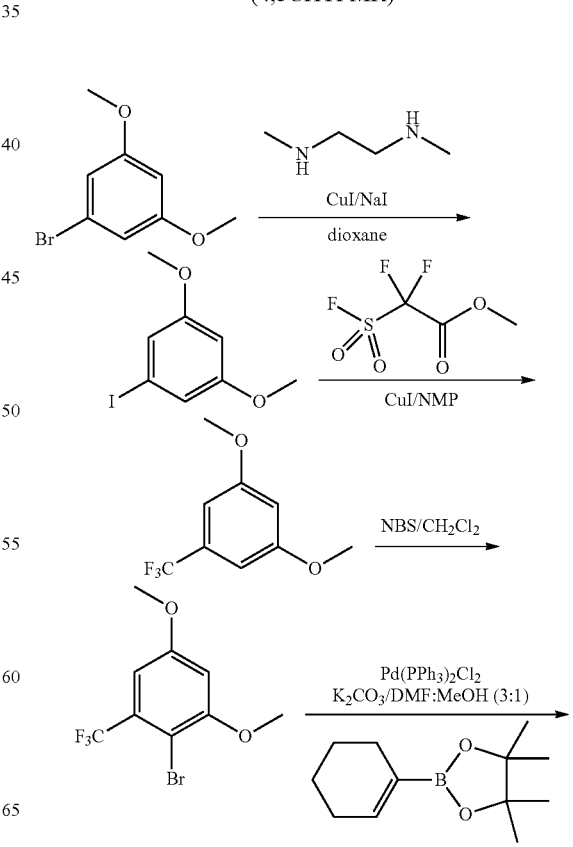

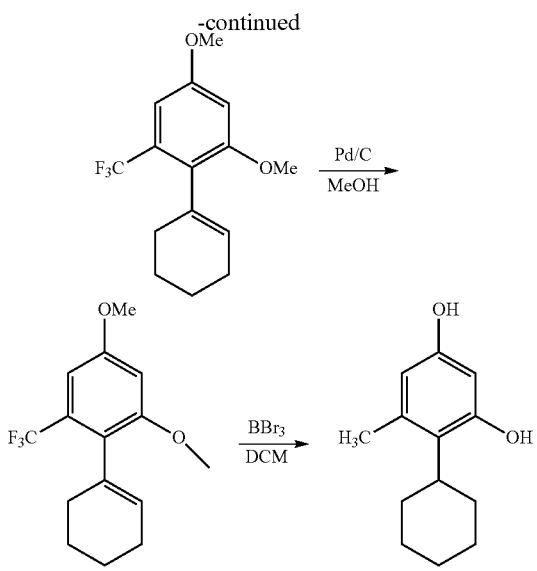

1-iodo-3,5-dimethoxy-benzene. A mixture of 1-bromo-3,5-dimethoxy-benzene (9.6 g, 44 mmol), CuI (0.7 g, 3.6 mmol), NaI (13.3 g, 88 mmol) and MeNHCH₂CH₂NHMe (0.78 mL) in 1,4-dioxane (80 mL) was degassed and filled with nitrogen in a sealed tube. The reaction mixture was heated at 120° C. for 20 h. The mixture was cooled to room temperature. Water (100 mL) was added, and the mixture was extracted with ethyl acetate (2×60 mL). The organic layers were washed with brine (50 mL), dried over sodium sulfate, and concentrated to give the title compound (10 g, 86%).

1,3-Dimethoxy-5-trifluoromethyl-benzene. A mixture of 1-iodo-3,5-dimethoxy-benzene (1.6 g, 6.0 mmol), difluorofluorosulfonyl-acetic acid methyl ester (3.1 mL, 24 mmol), and CuI (3.4 g, 18 mmol) in NMP (30 mL) was heated at 120° C. for 16 h, then the mixture was cooled to room temperature and water (50 mL) was added. The mixture was extracted with ethyl acetate (200 mL), washed with water (2×50 mL), and the organic layer was dried over sodium sulfate and concentrated. The crude product was purified by column chromatography (eluted with petroleum ether) to give the title compound (0.54 g, 44%).

2-bromo-1,5-dimethoxy-3-trifluoromethyl-benzene. A mixture of NBS (2.75 g, 16.9 mmol) and 1,3-dimethoxy-5-trifluoromethyl-benzene (3.5 g, 16.9 mmol) in dichloromethane was stirred at room temperature for 16 h. The mixture was concentrated and purified by column chromatography (eluted with petroleum ether:ethyl acetate=5:1) to obtain the title compound (4 g, 83%). $^1$H NMR (400 MHz, CDCl₃) δ6.84 (d, J=2.8 Hz, 1H), 6.63 (d, J=2.8 Hz, 1H), 3.91 (s, 3H), 3.84 (s, 3H). $^{19}$F NMR (360 MHz, CDCl₃) δ−62.7 (s).

2-cyclohex-1-enyl-1,5-dimethoxy-3-trifluoromethyl-benzene. To a mixture of 2-bromo-1,5-dimethoxy-3-trifluoromethyl-benzene (50 mg, 0.175 mmol), Pd(PPh₃)₂Cl₂ (12 mg, 0.0175 mmol), and K₂CO₃ (97 mg, 0.7 mmol) in mixed solvents (DMF/MeOH, 3:1, 1.2 mL) in a sealed tube was added 2-cyclohex-1-enyl-4,4,5,5-tetramethyl-[1,3,2]dioxaborolane (73 mg, 0.35 mmol). The tube was degassed and back-filled with N₂ (3×) and sealed under N₂. The tube was heated on oil bath to 100° C. for 6 h. After being cooled to room temperature, the reaction mixture was diluted with ethyl acetate/hexane and water. The organic layer was washed with brine, dried with Na₂SO₄, concentrated, and purified by prep TLC (ethyl acetate/hexanes, 8:2) to give the title compound (22 mg, 44%).

2-cyclohexyl-1,5-dimethoxy-3-trifluoromethyl-benzene. 2-Cyclohex-1-enyl-1,5-dimethoxy-3-trifluoromethyl-benzene (800 mg, 2.8 mmol) and MeOH (40 mL) were charged into a 200-mL round bottom flask fitted with a stir bar and septum cap. The solution was sparged with nitrogen for 5 min. To the mixture 10 wt % palladium on carbon (400 mg) was added. The flask was vacuumed and filled with a hydrogen balloon. The reaction mixture was stirred at 50° C. for 16 h. The reaction mixture was filtered and concentrated to give a residue, which was purified by silica gel column chromatography with ethyl acetate/hexanes to give the title compound (480 mg, 59%) as a white solid.

4-cyclohexyl-3-trifluoromethyl benzene-1,3-diol (4,5CHTFMR). To a solution of 4-cyclopentyl-1,3-dimethoxy-5-methylbenzene (480 mg, 1.67 mmol) in anhydrous CH₂Cl₂ (15 mL) at −78° in a dry ice/acetone bath was added boron tribromide (1.25 g, 5.0 mmol). The reaction mixture was stirred at −78° for 5 min and slowly warmed to room temperature overnight. The reaction mixture was quenched by slow addition of water (50 mL). The mixture was extracted with ether (3×). The combined organic extracts were washed with brine, dried over Na₂SO₄, and concentrated to give a residue, which was purified by silica gel column chromatography with ethyl acetate/hexanes to give the title compound (300 mg, 69%). LC-MS: 259 (M−1). $^1$H NMR (400 MHz, CDCl₃) δ6.69 (d, 1H), 6.40 (d, 1H), 5.11 (s, 1H), 5.07 (s, 1H), 2.88 (m, 1H), 1.99 (m, 2H), 1.69 (M, 4H), 1.29 (M, 4H).

Example 5

4-hexyl-5-methylbenzene-1,3-diol (4,5HMR)

The title compound may be prepared using methods analogous to those described in the Examples and general synthetic schemes. LC-MS: 209.0 (M+1). NMR (400 MHz, DMSO-d₆) δ8.87 (s, 1H), 8.79 (s, 2H), 6.07 (d, 1H), 5.98 (d, 1H), 2.34 (s, 2H), 2.07 (s, 3H), 1.23 (m, 8H), 0.83 (t, 3H).

Example 6

4-isopropyl-5-methylbenzene-1,3-diol (4,5HMR)

The title compound may be prepared using methods analogous to those described in the Examples and general synthetic schemes. $^1$H NMR (400 MHz, DMSO-d₆) δ8.83 (s, 1H), 8.78 (s, 1H), 6.05 (d, 1H), 5.94 (d, 1H), 3.04 (m, 1H), 2.09 (s, 3H), 1.20 (s, 3H), 1.18 (s, 3H).

Example 7

4-butyl-5-methylbenzene-1,3-dial (4,5BMR)

The title compound may be prepared using methods analogous to those described in the Examples and general synthetic schemes. LC-MS: 180.8 (M+1). $^1$H NMR (400 MHz, DMSO-d₆) δ8.87 (s, 1H), 8.78 (s, 1H), 6.07 (d, 1H), 5.98 (d, 1H), 2.37 (t, 2H), 2.07 (s, 3H), 1.28 (m, 4H), 0.85 (t, 3H).

Example 8

4-benzyl-5-methylbenzene-1,3-diol (4,5BnMR)

The title compound may be prepared using methods analogous to those described in the Examples and general synthetic schemes. $^1$H NMR (400 MHz, CDCl$_3$) δ7.27 (m, 2H), 7.17 (m, 3H), 6.30 (d, 1H), 6.22 (d, 1H), 4.73 (s, 1H), 4.68 (s, 1H), 3.97 (s, 2H), 2.21 (s, 3H).

Example 9

4-cyclopropyl-5-methylbenzene-1,3-diol (4,5CPrMR)

The title compound may be prepared using methods analogous to those described in the Examples and general synthetic schemes. $^1$H NMR (400 MHz, DMSO-d$_6$) δ8.85 (s, 1H), 8.66 (s, 1H), 6.04 (d, 1H), 5.99 (d, 1H), 2.17 (s, 3H), 1.35 (m, 1H), 0.75 (m, 2H), 0.45 (m, 2H).

Example 10

4-cyclopentylmethyl-5-methylbenzene-1,3-diol (4,5MCPMR)

The title compound may be prepared using methods analogous to those described in the Examples and general synthetic schemes. LC-MS: 207.0 (M+1). $^1$H NMR (400 MHz, DMSO-d$_6$) δ8.85 (s, 1H), 8.79 (s, 1H), 6.08 (s, 1H), 5.99 (s, 1H), 2.39 (d, 2H), 2.08 (s, 3H), 1.99 (m, 1H), 1.52 (m, 6H), 1.18 (m, 2H).

Example 11

4-cyclopentyl-5-methylbenzene-1,3-diol (4,5CPMR)

The title compound may be prepared using methods analogous to those described in the Examples and general synthetic schemes. LC-MS: 193.1 (M+1). $^1$H NMR (400 MHz, CDCl$_3$) δ6.23 (d, 1H), 6.13 (d, 1H), 4.63 (s, 1H), 4.58 (s, 1H), 3.25 (m, 1H), 2.27 (s, 3H), 1.88 (m, 6H), 1.67 (m, 2H).

Example 12

4-ethyl-5-methylbenzene-1,3-diol (4,5EMR)

The title compound may be prepared using methods analogous to those described in the Examples and general synthetic schemes. LC-MS: 152.8 (M+1). $^1$H NMR (400 MHz, DMSO-d$_6$) δ8.87 (s, 1H), 8.76 (s, 1H), 6.08 (s, 1H), 5.99 (s, 1H), 2.38 (q, 2H), 2.08 (s, 3H), 0.93 (t, 3H).

Example 13

4-sec-butyl-5-methylbenzene-1,3-diol (4,5sBMR)

The title compound may be prepared using methods analogous to those described in the Examples and general synthetic schemes. LC-MS: 181.15 (M+1). $^1$H NMR (400 MHz, CD$_3$OD) δ6.21 (s, 1H), 6.11 (s, 1H), 4.80 (m, 2H), 2.92 (m, 1H), 1.80 (m, 2H), 1.26 (d, 3H), 0.82 (t, 3H).

Example 14

4-(1-phenylethyl)-5-methylbenzene-1,3-diol (4,5PEMR)

The title compound may be prepared using methods analogous to those described in the Examples and general synthetic schemes. LC-MS: 229.0 (M+1). $^1$H NMR (400 MHz, CDCl$_3$) δ7.32 (m, 3H), 7.25 (m, 2H), 6.29 (d, 1H), 6.13 (d, 1H), 4.64 (s, 1H), 4.50 (m, 2H), 2.32 (s, 3H), 1.63 (t, 3H).

Example 15

4-(2,2,2-trifluoroethyl)-5-methylbenzene-1,3-diol (4,5TFEMR)

The title compound may be prepared using methods analogous to those described in the Examples and general synthetic schemes. $^1$H NMR (400 MHz, CD$_3$OD) δ6.16 (s, 2H), 3.43 (q, 2H), 2.20 (s, 3H).

Example 16

4-cyclohexyl-5-fluorobenzene-1,3-diol (4,5EFR)

The title compound may be prepared using methods analogous to those described in the Examples and general synthetic schemes. $^1$H NMR (DMSO-d$_6$, 400 MHz) δ: 9.48 (s, 1H), 9.33 (s, 1H), 6.12 (dd, J=2.3, 1.3 Hz, 1H), 5.96 (dd, J=12, 2.3 Hz, 1H), 2.85 (qd, J=7.4, 1.2 Hz, 2H), 1.01 (t, J=7.4 Hz, 3H).

Example 17

2-Benzyl-1,5-dihydroxy-3-trifluoromethyl-benzene (4,5BNTFMR)

LC-MS: 267 (M−1). $^1$H NMR (400 MHz, CDCl$_3$) δ7.14-7.28 (m, 5H), 6.81 (d, J=2.0 Hz, 1H), 6.52 (s, 1H), 5.11 (s, 1H), 4.98 (s, 1H), 4.11 (s, 2H). $^{19}$F NMR (360 MHz, CDCl$_3$) δ−59.7 (s).

Example 18

Mushroom Tyrosinase Inhibition Assay

10 μM compound, 300 μM L-Tyrosine, and 84 units/mL of mushroom tyrosinase (Sigma T3824) were combined into 0.05 M potassium monophosphate buffer at pH=6.5, and incubated for 15 min at room temperature. Absorbance was recorded at 490 nm. % tyrosinase inhibition was calculated as follows: $(Abs_{DMSO}-Abs_{cmpd})/Abs_{DMSO} \times 100$. The assay was performed for various compounds described herein, as well as for control compounds 4-ethyl resorcinol (4ER), 4-isopropylresorcinol (4IPR), 4-hexylresorcinol (4HR), 4-cyclohexylresorcinol (4CHR), 5-methylresorcinol (5MR), kojic acid (KA), and hydroquinone (HQ), structures of which are shown below. Results are shown in Table 1.

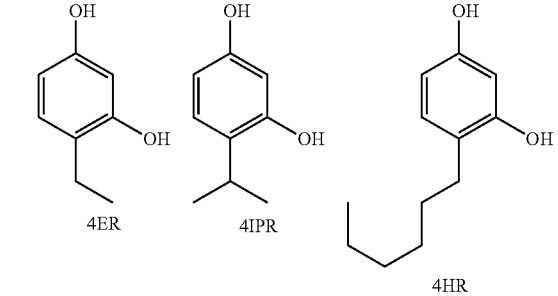

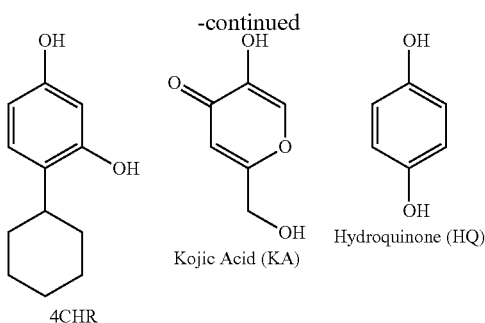

4CHR     Kojic Acid (KA)     Hydroquinone (HQ)

TABLE 1

Mushroom Tyrosinase (% remaining enzyme activity)

| Compound | % TYR Activity |
|---|---|
| 4,5CHMR | 22 |
| 4,5 BMR | 18 |
| 4,5BnMR | 97 |
| 4,5TFEMR | 103 |
| 4,5sBMR | 100 |
| 4,5HMR | 10 |
| 4,5CPMR | 71 |
| 4,5CPrMR | 30 |
| 4,5PEMR | 105 |
| 4,5EMR | 93 |
| 4,5IPMR | 108 |
| 4,5MCPMR | 32 |
| 4,5ETFMR | 102 |
| 4,5CHTFMR | 100 |
| 4,5BnTFMR | 93 |
| 4,5EFR | 3 |
| 4,5CHFR | 1 |
| 4ER | 2 |
| 4IPR | 1 |
| 4HR | 1 |
| 4CHR | 0 |
| 5MR | 100 |
| Hydroquinone | 100 |
| Kojic Acid | 84 |

Example 19

Mammalian Tyrosinase Inhibition Assay

B16F1 cells are grown in Dulbecco's Modified Eagle Medium (DMEM) 10% FBS, P/S at 10% $CO_2$ and 37° C. to 90% confluency. Cell lysate is prepared with 150 mM NaCl; 20 mM Tris-HCl, pH=7.4; and 1% Triton-X100. The assay is conducted in buffer (0.05M potassium monophosphate buffer, pH=6.5, 600 uM L-Tyrosine, 15 uM L-Dopa, 0.325 mg/mL B16F1 cell lysate) with 10 µM compound. After mixing, the reaction mixture is incubated at 37° C. for 8 h and absorbance measured at 490 nm. % tyrosinase inhibition is calculated as follows: $(Abs_{DMSO}-Abs_{cmpd})/Abs_{DMSO} \times 100$.

Example 20

B16 Melanin Assay

B16F1 cells were grown in phenol free DMEM 10% FBS, P/S at 10% $CO_2$ and 37° C. After trypsinization, cells were seeded at 3,000 cells per well in a 96-well plate and allowed to attach overnight. 1 mM Theophylline was used to stimulate melanogenesis, and the compound of interest was added. After 72 h growth at 10% $CO_2$ and 37° C., media absorbance was measured at 405 nm and corrected for cellular viability measured with Calcein-AM. % melanin content was calculated as follows: $(Abs_{DMSO}/Calcein_{DMSO}-Abs_{cmpd}/Calcein_{cmpd})/Abs_{DMSO}/Calcein_{DMSO} \times 100$. The assay was performed for various compounds described herein, as well as for control compounds 4ER, 4IPR, 4HR, 4CHR, 5MR kojic acid, and hydroquinone. Results are shown in Table 2.

TABLE 2

B16 Media Melanin (% Melanin)

| Compound | % Melanin B16 |
|---|---|
| 4,5CHMR | 58 |
| 4,5 BMR | 55 |
| 4,5BnMR | 86 |
| 4,5TFEMR | 90 |
| 4,5sBMR | 76 |
| 4,5HMR | 78 |
| 4,5CPMR | 61 |
| 4,5CPrMR | 62 |
| 4,5PEMR | 87 |
| 4,5EMR | 69 |
| 4,5IPMR | 71 |
| 4,5MCPMR | 90 |
| 4,5ETFMR | 68 |
| 4,5CHTFMR | 65 |
| 4,5BnTFMR | 82 |
| 4,5EFR | 87 |
| 4,5CHFR | 51 |
| 4ER | 48 |
| 4IPR | 77 |
| 4HR | 71 |
| 4CHR | 63 |
| 5MR | 100 |
| Hydroquinone | 100 |
| Kojic Acid | 100 |

Example 21

Melanocyte-HaCaT Co-Culture Assay

Darkly pigmented human neonatal epidermal melanocytes (HEMn-DP, Invitrogen) were grown in Medium 254 with HMGS-2 supplement and P/S at 37° C. and 5% $CO_2$. HaCaT cells were grown in DMEM, 10% FBS, P/S at 37° C., 5% $CO_2$. Co-culture was conducted in 50% melanocyte media+50% keratinocyte media (EpiLIfe with EDGS, P/S). Cells were plated in the co-culture media at 40K (HaCaT) and 30K (HEMn-DP) per well in a 24-well plate. After 24 h of incubation at 37° C. and 5% $CO_2$, media was changed to M153 (MCDB153 Sigma M7403 with $NaHCO_3$ pH to 7.1, 2 mM Tyrosine, 10 nM NDP-aMSH, 3 ng/mL bFGF, 2.8 ug/mL Hydrocortisone, 10 ug/mL Insulin, 10 ug/mL Transferrin, and P/S), treated with compound, and incubated for 72 h at 37° C. and 5% $CO_2$. After measuring cellular viability with Calcein-AM (RFU Ex/Em=488/525 nm), cells were lysed at 1 h at 65° C. with 1N NaOH+10% DMSO. Absorbance of cleared lysate was measured at 405 nm and 660 nm. % melanin was calculated as follows: $((Abs405_{DMSO}-Abs660_{DMSO})/Calcein_{DMSO}-(Abs405_{comp}-Abs660_{comp})/Calcein_{comp}))/(Abs405_{DMSO}-Abs660_{DMSO})/Calcein_{DMSO} \times 100$. At 10 µM concentration, % cellular melanin was 42% in the presence of compound 4,5CHMR.

Example 22

Mattek 3D Skin Equivalents

MelanoDerm (Mel-300-B) assay was conducted according to the manufacturer's instruction (MatTek Corporation). Every other day, the test articles were administered into the EPI-100-NMM-113 culture medium, and positive control, 25 uL of 2% Kojic acid was applied topically. After 14 days, tissue viability and melanocyte morphology were visually verified and tissue melanin was extracted and quantitated against a standard curve. % melanin was calculated as follows: (Melanin$_{DMSO}$−Melanin$_{comp}$)/Melanin$_{DMSO}$×100. The assay was performed for various compounds described herein, as well as for control compounds 4ER, 4IPR, 4HR, 4CHR, kojic acid, and hydroquinone. Results are shown in Table 3.

TABLE 3

MatTek Assay (% Melanin)

| Compound | % Melanin 3D EpiDerm | |
|---|---|---|
| | 30 µM | 10 µM |
| 4,5CHMR | 44 | 66 |
| 4,5 BMR | 64 | 81 |
| 4,5BnMR | 61 | 82 |
| 4,5TFEMR | 72 | 81 |
| 4,5sBMR | 67 | 75 |
| 4,5HMR | 68 | 77 |
| 4,5CPMR | 55 | 65 |
| 4,5CPrMR | 82 | 99 |
| 4,5PEMR | 62 | 98 |
| 4,5EMR | 79 | 102 |
| 4,5IPMR | 72 | 102 |
| 4,5MCPMR | 72 | 94 |
| 4,5ETFMR | 66 | 81 |
| 4,5CHTFMR | | 89 |
| 4,5BnTFMR | 75 | 93 |
| 4,5CHFR | 81 | 87 |
| 4ER | 61 | 84 |
| 4IPR | 46 | 71 |
| 4HR | 72 | 93 |
| 4CHR | 36 | 65 |
| Hydroquinone | 92 | 94 |
| Kojic Acid | 100 | 100 |
| KA topical | 75 | |

Example 23

Clinical Evaluation for Dark Circles

Female subjects with mild to moderate dark circles under their edges are recruited for the study after providing informed consent. The study is conducted in accordance with all applicable government regulations and institutional policies. Both an expert grader and the subjects evaluate the severity of the dark circles under their eyes prior to application of test products. A composition containing one or more compounds as described herein is topically applied to the skin area around one eye and a composition not containing the compounds described herein around the opposite eye as a control. Treatment assignments are randomized across the panel, and neither the subject nor the grader has knowledge of the treatment code. One hour after product application, both the grader and subject separately evaluate the appearance of the dark circles under the eyes.

Example 24

Clinical Evaluation for Puffiness

A set of female subjects with puffiness under their eyes is recruited after providing informed consent. The study is conducted in accordance with all applicable government regulations and institutional policies. A composition containing a compound described herein is applied under one eye, and a composition with no compound as described herein is applied under the other eye as a control. The subjects use the product for 4 weeks, returning at week 2 for another dermatological evaluation. After 2 and 4 weeks of product use, both the subjects and the dermatologist evaluate the improvement in the puffiness of the eyes compared with the baseline observations.

Example 25

Clinical Evaluation for Aging Signs

A set of male and female subjects is recruited after providing informed consent. The study is conducted in accordance with all applicable government regulations and institutional policies. Expert graders trained in visual and tactile evaluations assess the different aging signs of the face of each subject by grading on a semi-structured scale. Each subject is characterized by a quantitative profile of his or her aging signs and two expert graders evaluate each parameter at each time point. A composition containing a compound described herein is applied to one section of the face, and a composition with no compound as described herein is applied to another section of the face as a control. The subjects use the product for 4 weeks, returning at week 2 and week 4 for an evaluation by the graders.

Mean values and standard deviation are calculated, as well as variations of the parameter relative to before application (expressed in percentage). A Paired Student's t test is used to determine the significance of the results.

While the present compositions and methods have been described with reference to the specific variations thereof, it should be understood by those skilled in the art that various changes may be made and equivalents may be substituted without departing from the true spirit and scope of the compositions and methods described herein. In addition, many modifications may be made to adapt a particular situation, material, composition of matter, process, process step or steps, to the objective, spirit and scope of the compounds and methods described herein. All patents and publications cited above are hereby incorporated by reference.

What is claimed is:

1. A cosmetic or dermatological composition comprising:
   (a) from 0.01% to about 10% of one or more resorcinol compounds selected from the group consisting of:

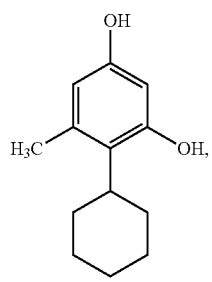

Compound 5 referred to as 4,5-CHMR

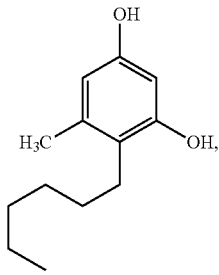

referred to as 4,5HMR,

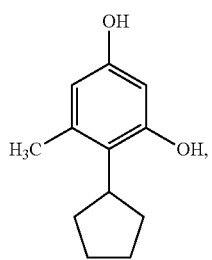

referred to as 4,5CPMR, or

Compound 1

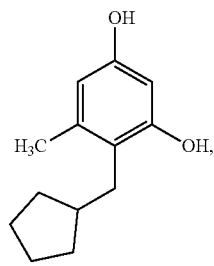

Compound 4

Compound 3 referred to as 4,5MCPMR;
or a pharmaceutically acceptable salt thereof; or mixtures thereof;
   (b) a dermatologically acceptable carrier; and
   (c) wherein the composition is in the form of a product selected from the group consisting of gel, lotion, or cream.

2. The composition of claim 1, further comprising a compound selected from the group consisting of sunscreens; retinoids; hydroxyacids; fatty acids, non-toxic metal salts of naturally occurring amino acids or of hydroxyalkyl acids; botanical extracts, salicylic acid, benzoyl peroxide, anti-inflammatory agents, ascorbic acid, vitamins B, and mixtures thereof.

3. The composition of claim 2, wherein the composition comprises retinyl propionate.

4. The composition of claim 1, wherein the composition comprises vitamins B.

5. The composition of claim 2, wherein the composition comprises a sunscreen.

\* \* \* \* \*